(12) United States Patent
Eason

(10) Patent No.: US 8,492,158 B2
(45) Date of Patent: Jul. 23, 2013

(54) ELECTROCHEMICAL LABELS DERIVED FROM SIDEROPHORES

(75) Inventor: Robert G. Eason, Los Gatos, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 832 days.

(21) Appl. No.: 12/059,744

(22) Filed: Mar. 31, 2008

(65) Prior Publication Data

US 2009/0246763 A1 Oct. 1, 2009

(51) Int. Cl.
*G01N 33/20* (2006.01)

(52) U.S. Cl.
USPC ............................................................ 436/84

(58) Field of Classification Search
None
See application file for complete search history.

(56) References Cited

U.S. PATENT DOCUMENTS

| | | | | |
|---|---|---|---|---|
| 4,433,288 | A * | 2/1984 | Moore | 324/754.23 |
| 5,094,864 | A * | 3/1992 | Pinon et al. | 426/233 |
| 6,071,699 | A | 6/2000 | Meade et al. | |
| 6,676,816 | B2 | 1/2004 | Mao et al. | |
| 7,045,310 | B2 | 5/2006 | Buck, Jr. et al. | |
| 7,087,148 | B1 | 8/2006 | Blackburn et al. | |
| 2003/0232354 | A1 | 12/2003 | Yu et al. | |
| 2005/0058604 | A1 | 3/2005 | Raymond et al. | |
| 2005/0277120 | A1 | 12/2005 | Gao et al. | |
| 2007/0001166 | A1 | 1/2007 | Tao et al. | |
| 2007/0099211 | A1 | 5/2007 | Aivazachvili et al. | |

FOREIGN PATENT DOCUMENTS

| | | |
|---|---|---|
| WO | 03085082 A2 | 10/2003 |
| WO | WO 2009/134570 A2 | 11/2009 |
| WO | WO 2009/134570 A3 | 12/2010 |

OTHER PUBLICATIONS

Elandalloussi et al ('Effect of desferioxamine and 2,2'-bipyridyl on the proliferation of Perkinsus atlanticus' 2003 Biomolecular Engineering v20 pp. 349-354).*
Purdue Chemistry web site (retrieved from http://www.chem.purdue.edu/gchelp/cchem/whatis.html on Jul. 28, 2011, 3 pages).*
Raymond, et al., "Enterobactin: An archetype for microbial iron transport," PNAS, vol. 100, No. 7 (Apr. 1, 2003), pp. 3584-3588.
PCTUS0939008, "International Preliminary Report on Patentability mailed on Oct. 28, 2010".
PCTUS0939008, "International Search Report and Written Opinion Mailed on Oct. 13, 2010".

* cited by examiner

*Primary Examiner* — Cecilia J Tsang
*Assistant Examiner* — Ronald Niebauer

(57) ABSTRACT

Disclosed are tri-nuclear metal complexes and salts thereof, such as tri-nuclear osmium or ruthenium complexes or salts thereof, suitable for use as electrochemical labels. Also disclosed are oligonucleotide probes with an attached electrochemical label, methods of nucleic acid amplification, methods of sequencing, and kits for nucleic acid amplification and sequencing having oligonucleotide probes including an electrochemical label. The electrochemical labels are synthesized from siderophores.

3 Claims, 6 Drawing Sheets

Desferrioxamine B desferrichrome A desferrirhodin salmochelin 2

ELECTROCHEMICAL LABELS DERIVED FROM SIDEROPHORES

FIELD

The present teachings relate generally to electrochemical labels suitable for use in nucleic acid amplification and sequencing techniques. The present teachings herein relate also to metal-based electrochemical labels, probes including the metal-based electrochemical labels, and methods of nucleic acid amplification or sequencing utilizing the metal-based electrochemical labels. The electrochemical labels are derived from siderophores, and can include osmium, ruthenium, or another metal as discussed herein.

BACKGROUND

A number of nucleic acid amplification methods, such Polymerase Chain Reaction (PCR), have been developed over the years that generate a single-stranded DNA or RNA product during cycling. This single-stranded product can be potentially detected in real-time or in end-point-type assays using an amplicon-specific complementary oligonucleotide cleavable probe, such as a TaqMan® probe or similar cleavable probe.

TaqMan® probes and similar cleavable probes depend on the 5'-nuclease activity of the DNA polymerase used for PCR to hydrolyze an oligonucleotide that is hybridized to the target amplicon. TaqMan®-type cleavable probes are oligonucleotides that generally include a reporter moiety, such as a fluorescent reporter dye attached to the 5' end and a quencher moiety coupled to the 3' end. These probes are designed to hybridize to an internal region of a PCR product. In the unhybridized state, the proximity of the fluorescent tag and the quencher attenuates the generation of a fluorescent signal from the probe. During PCR, when the polymerase replicates a template on which a TaqMan® probe is bound, the 5'-nuclease activity of the polymerase cleaves the probe. This decouples the fluorescent and quenching dyes and quenching no longer occurs. Thus, fluorescence increases in each cycle, proportional to the amount of probe cleavage.

Reporter moieties other than fluorescent-based reporter moieties can also be utilized in nucleic acid amplification techniques and can allow for portable, low-energy consumption microfluidic devices to be utilized. For example, electrochemical reporter moieties, such as ferrocene-based reporter moieties, can be utilized in these techniques. Although electrochemical reporter moieties can offer similar sensitivity and specificity as compared to optical-type reporter moieties, they have generally been more problematic at elevated temperatures (such as those encountered during PCR) due to signal degradation. Additionally, ferrocene-type electrochemical reporter moieties are generally less soluble and can have less chemical stability in the desired oxidation states suitable for use as reporter moieties.

The problems associated to date with the use of electrochemical reporter moieties in nucleic acid amplification and sequencing techniques are obviated by the present disclosure.

SUMMARY

The present teachings provide tri-nuclear metal complexes and salts thereof, such as tri-nuclear osmium (II) complexes and salts thereof, that are synthesized from siderophores. These tri-nuclear metal complexes are suitable for use as electrochemical labels in, for example, cleavable DNA sequencing probes. The electrochemical labels, and the DNA sequencing probes containing the electrochemical labels, can be utilized in nucleic acid amplification methods, including PCR methods, and in kits for nucleic acid amplification methods, in sequencing methods and kits, and can be especially suitable for use in electrochemical detection methods used in TaqMan®-like assays.

The electrochemical labels and processes disclosed herein allow for multiple labels to be introduced onto a single electrochemical reporter moiety in a single synthetic step. This results in less overall degradation and loss of the electrochemical label during usage. Conventional methods have required sequential addition of a single label onto an electrochemical reporter moiety resulting in degradation and loss of label.

In some embodiments, the present teachings provide a tri-nuclear metal complex comprising structure (I), structure, (II), structure (III) or structure (IV), or salt thereof:

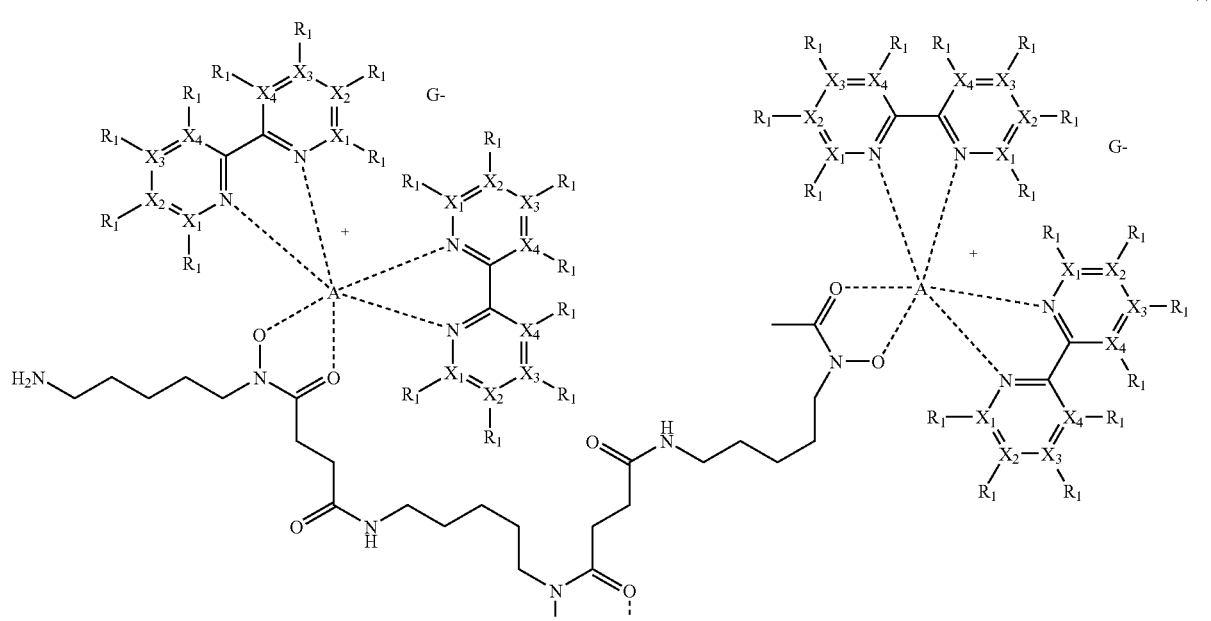

(I)

-continued
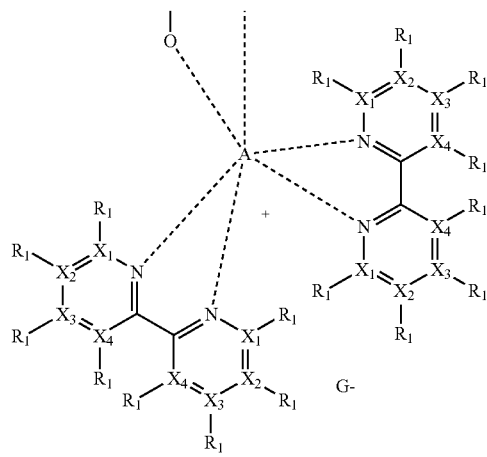
(II)
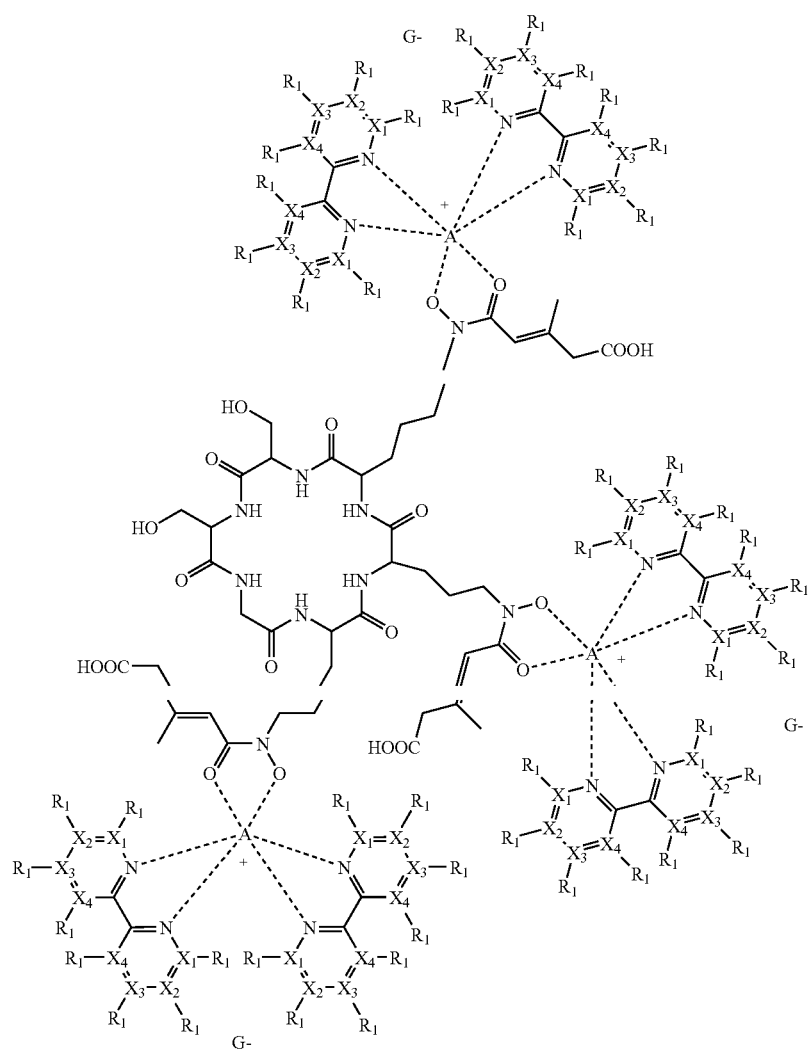

(III)
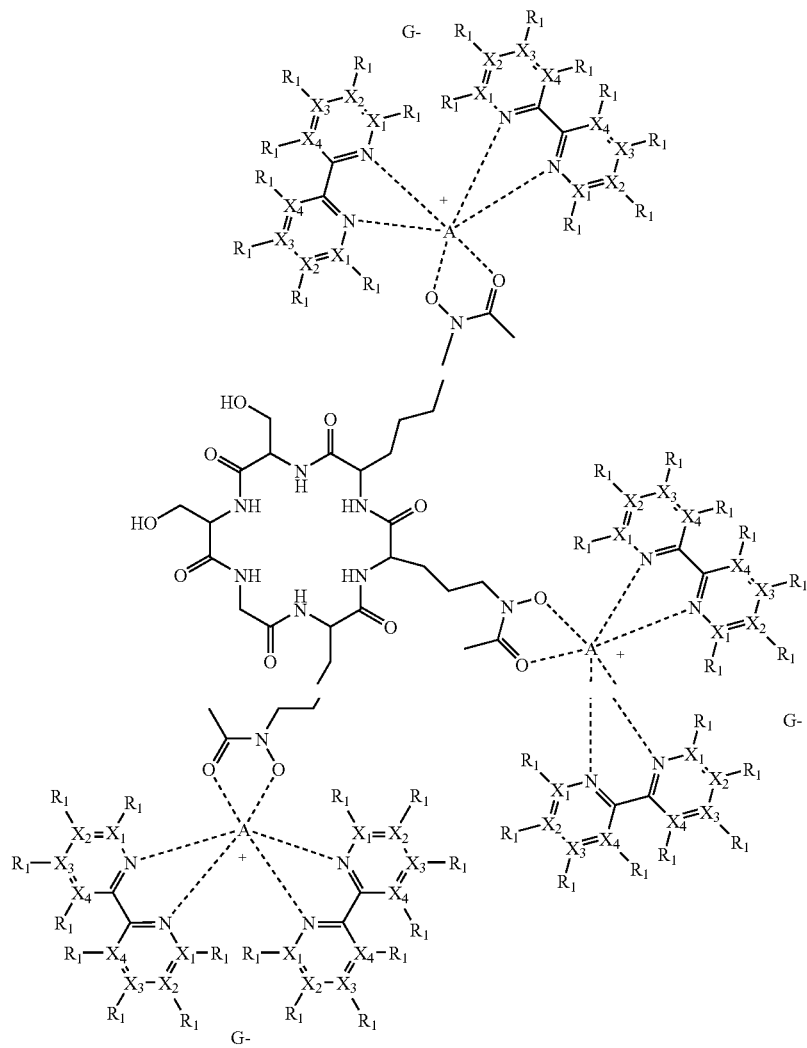
(IV)
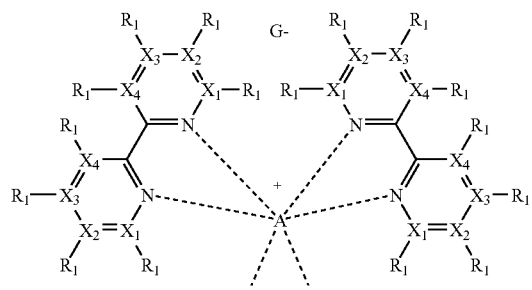

-continued

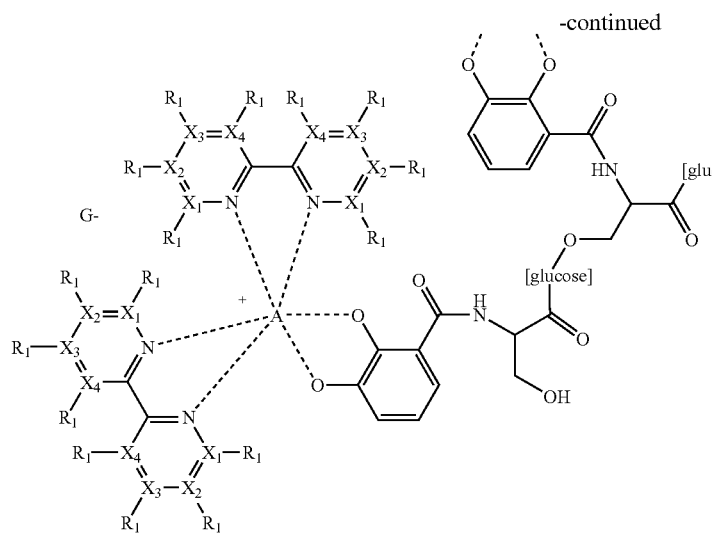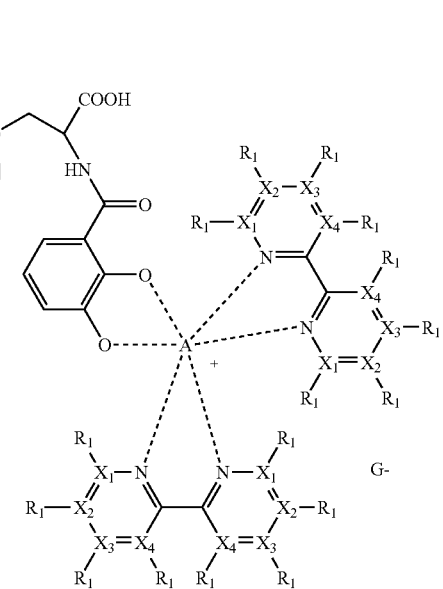

wherein:

A is Os, Ru, Fe, V, Cr, Mn, or Co;

$X^1, X^2, X^3, X^4$ are independently selected from C or N; when $X^1$ is N the $R^1$ corresponding to that $X^1$ is omitted; when $X^2$ is N, the $R^1$ corresponding to that $X^2$ omitted; when $X^3$ is N, the $R^1$ corresponding to that $X^3$ is omitted; and when $X^4$ is N, the $R^1$ corresponding to that $X^4$ is omitted;

$R^1$ is H, $C_1$-$C_8$ alkyl, alkenyl or alkynyl and can be substituted with a hetero atom, $C_1$-$C_8$ substituted phenyl, alkoxy, alkylthio, $C_1$-$C_{10}$ N-alkylamino, N,N-dialkylamino, N,N,N-trialkylammonium, N-alkylaminocarbonyl, N,N-dialkylaminocarbonyl, alkylcarboxylamino, fluoro, chloro, bromo, iodo, fluoroalkyl, chloroalkyl, bromoalkyl, iodoalkyl, O-alkylcarbamoyl, N-alkylcarbamoyl, nitro, cyano, carboxyl, formyl, alkylcarbonyl, alkoxycarbonyl, hydroxyl, hydrazido, aryl, or aryl alkyl; and $G^-$ is a monovalent counterion that can be selected from $PF_6^-$, $TFA^-$, $OAc^-$, $Cl^-$ and $Br^-$.

In other embodiments, the present teachings provide a probe comprising an oligonucleotide labeled with an electrochemical label, the probe comprising structure (V), structure (VI), structure (VII) or structure (VIII), or a salt thereof:

(V)

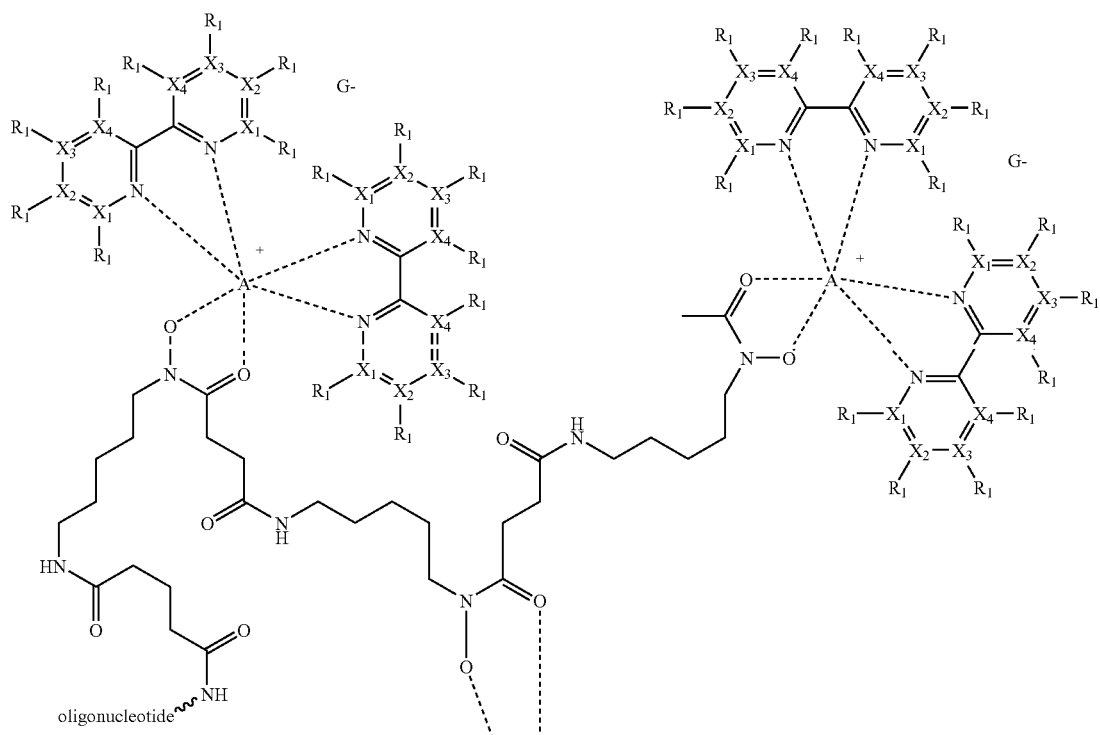

-continued
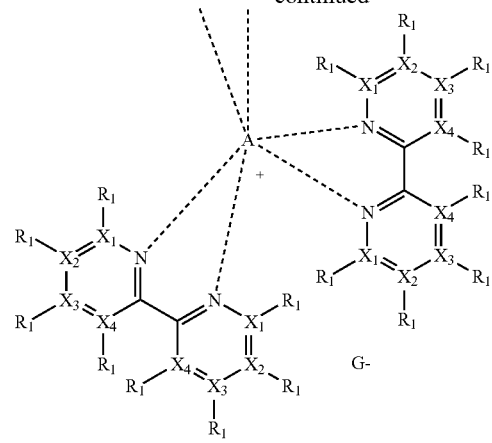
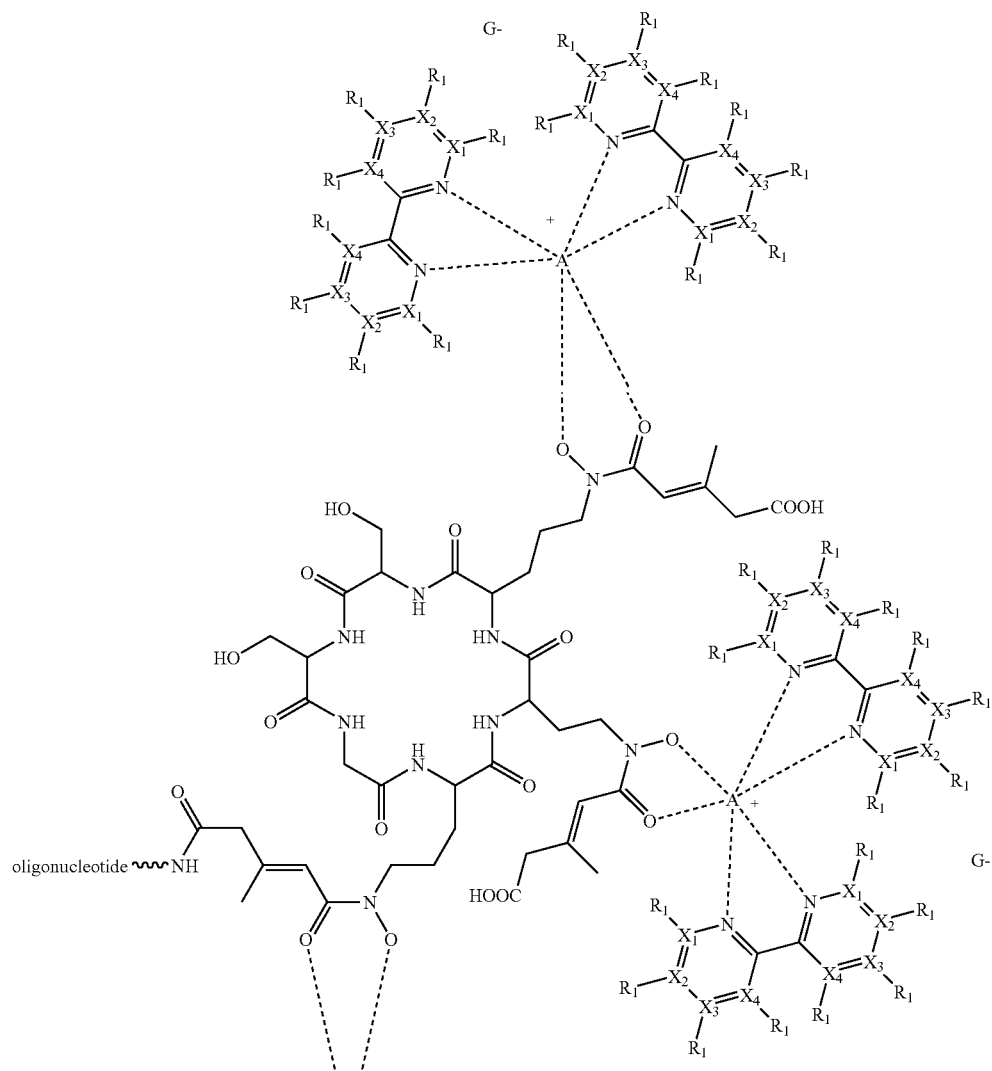
(VI)

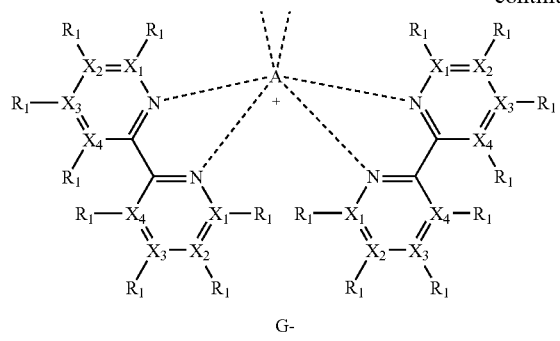
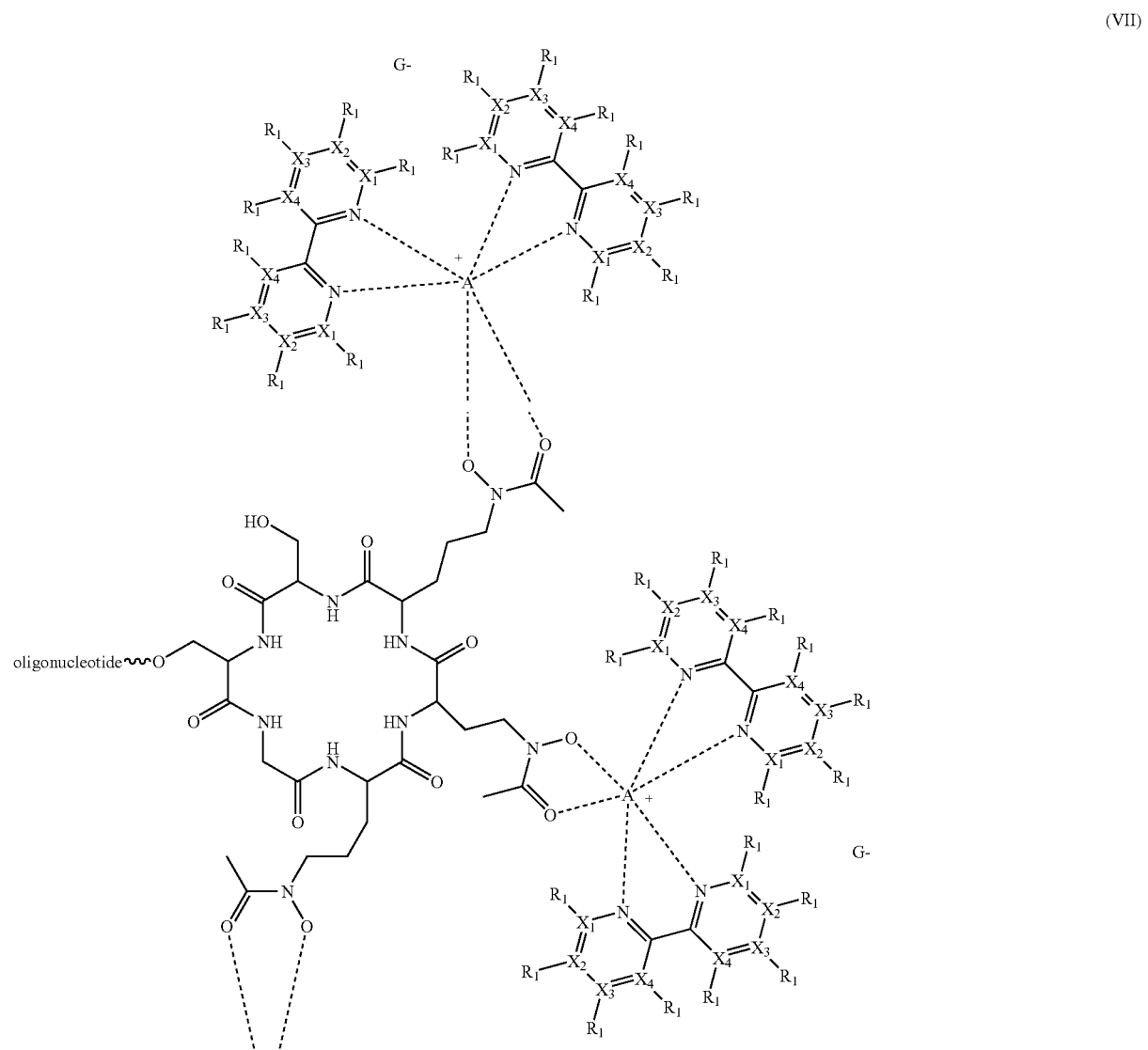
(VII)

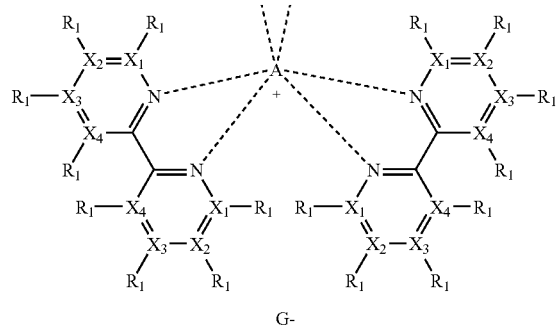

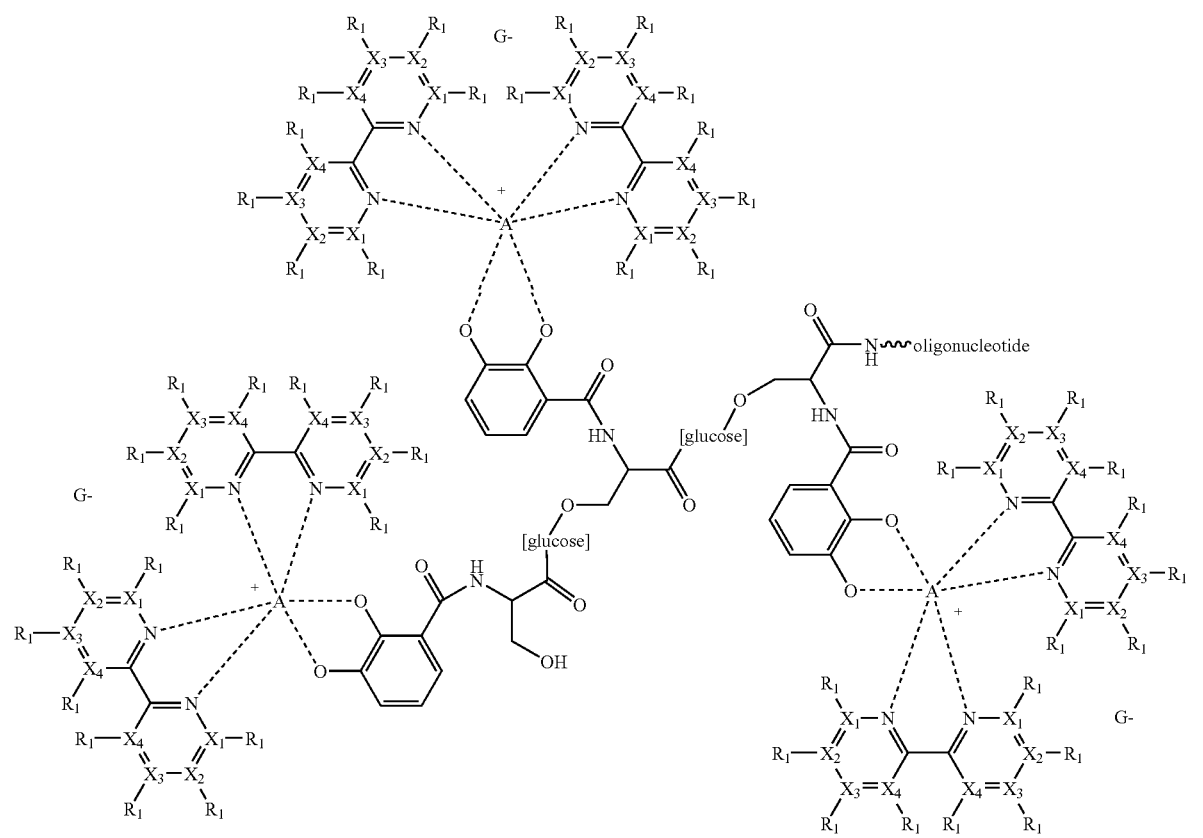

(VIII)

wherein
A is Os, Ru, Fe, V, Cr, Mn, or Co;
$X^1, X^2, X^3, X^4$ are independently selected from C or N; when $X^1$ is N, the $R^1$ corresponding to that $X^1$ is omitted; when $X^2$ is N, the $R^1$ corresponding to that $X^2$ omitted; when $X^3$ is N, the $R^1$ corresponding to that $X^3$ is omitted; and when $X^4$ is N, the $R^1$ corresponding to that $X^4$ is omitted;
$R^1$ is H, $C_1$-$C_8$ alkyl, alkenyl or alkynyl and can be substituted with a hetero atom, $C_1$-$C_8$ substituted phenyl, alkoxy, alkylthio, $C_1$-$C_{10}$ N-alkylamino, N,N-dialkylamino, N,N,N-trialkylammonium, N-alkylaminocarbonyl, N,N-dialkylaminocarbonyl, alkylcarboxylamino, fluoro, chloro, bromo, iodo, fluoroalkyl, chloroalkyl, bromoalkyl, iodoalkyl, O-alkylcarbamoyl, N-alkylcarbamoyl, nitro, cyano, carboxyl, formyl, alkylcarbonyl, alkoxycarbonyl, hydroxyl, hydrazido, aryl or aryl alkyl;
$G^-$ is a monovalent counterion that can be selected from $PF_6^-$, $TFA^-$, $OAc^-$, $Cl^-$ and $Br^-$; and 〰️ is a linker between the electrochemical label and an oligonucleotide.

The linker between the electrochemical label and the oligonucleotide can be any conventional moiety known to one of ordinary skill in the art that can link an electrochemical label to an oligonucleotide, such as a moiety that links at the 5' end of the oligonucleotide. Examples include:

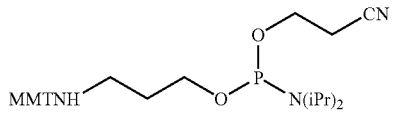

and

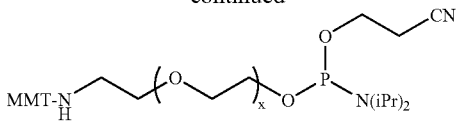

wherein x is 1, 2, 3, 4, 5, 6, 7, 8, 9, 10, 11, 12, 13, 14, 15, 16, 17, 18, 19, or 20.

In other embodiments, the present teachings provide a nucleic acid amplification method comprising providing a probe comprising an oligonucleotide labeled with an electrochemical label; displacing the electrochemical label from the oligonucleotide probe during amplification; and detecting the displaced electrochemical label; wherein the probe comprises structure (V), structure (VI), structure (VII), or structure (VIII), or a salt thereof, as described above.

In other embodiments, the present teachings provide a kit for polynucleotide amplification wherein the kit comprises a first primer and a second primer; a polymerase; and a probe comprising an oligonucleotide labeled with an electrochemical label, the probe comprising structure (V), structure (VI), structure (VII), or structure (VIII), or a salt thereof, as described above.

In other embodiments, the disclosure provides a method of preparing a tri-nuclear metal complex or salt thereof comprising reacting a siderophore with a bis-bipyridinyl or bis-biheterocycle osmium or ruthenium carbonate complex or salt thereof, or other metal containing complex or salt thereof, as disclosed herein.

These and other features of the present teachings are set forth herein.

DRAWINGS

The skilled artisan will understand that the drawings, described below, are for illustration purposes only. The drawings are not intended to limit the scope of the present teachings in any way.

DESCRIPTION OF VARIOUS EMBODIMENTS

Figure 1:
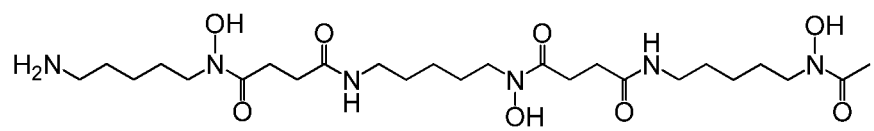
FIGS. 1 and 2 show the chemical structures for various siderophores.
Figure 1:
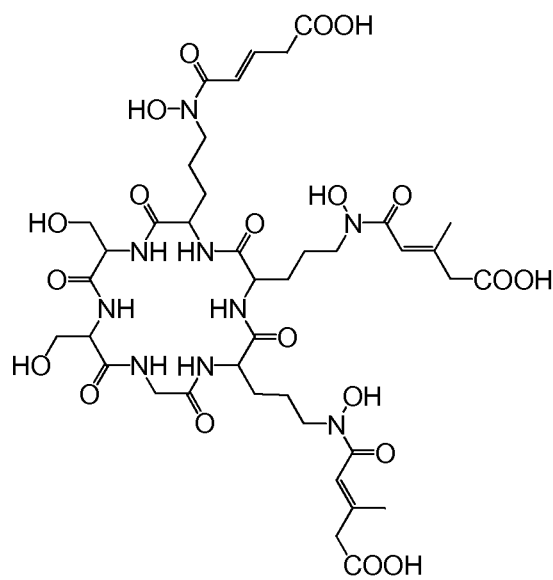
Figure 1:
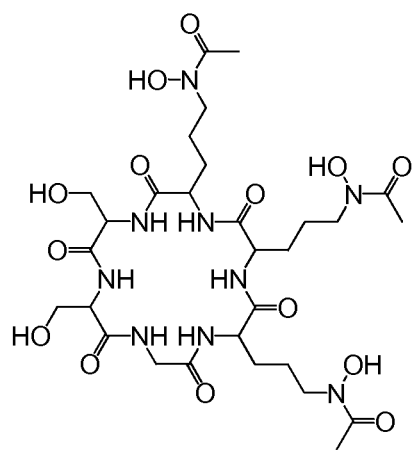

Before describing the present disclosure in detail, it is to be understood that this disclosure is not limited to specific compositions, kits, process steps, or equipment, as such can vary. It should also be understood that the terminology used herein is for the purpose of describing various embodiments only, and is not intended to be limiting. Methods recited herein can be carried out in any order of the recited events that is logically possible, as well as the recited order of events. Furthermore, where a range of values is provided, it is understood that every intervening value, between the upper and lower limit of that range and any other stated or intervening value in that stated range is encompassed within the disclosure. Also, it is contemplated that any optional feature of the inventive variations described can be set forth and claimed independently, or in combination with any one or more of the features described herein. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Unless defined otherwise below, all technical and scientific terms used herein have the same meaning as commonly understood by one of ordinary skill in the art to which this disclosure belongs. Certain elements are defined herein for the sake of clarity.

It is noted that, as used in this specification and the appended claims, the singular forms "a", "an" and "the" include plural referents unless the context clearly dictates otherwise. Thus, for example, reference to "a polynucleotide" includes a plurality of polynucleotides and the like.

In describing and claiming the present disclosure, the following terminology will be used in accordance with the definitions set out below.

"Alkyl" refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl, cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc., and the like. Included are linear or branched hydrocarbon chains including from 1 to 20 carbon atoms which can be substituted with a halogen, heteroatom and/or aryl substituents.

"Alkenyl" refers to an unsaturated branched, straight-chain or cyclic alkyl radical having at least one carbon=carbon double bond derived by the removal of one hydrogen atom from a single carbon atom of a parent alkene. The radical can be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc., and the like.

"Alkynyl" includes unsaturated aliphatic groups analogous in length and possible substitution to the alkyls described above, but which contain at least one triple bond. For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term alkynyl includes both "unsubstituted alkynyls" and "substituted alkynyls", the latter of which refers to alkynyl groups having substituents replacing a hydrogen on one or more carbons of the hydrocarbon backbone.

"Polynucleotide" refers to linear polymers of natural nucleotide monomers or analogs thereof, including, for example, double- and single-stranded deoxyribonucleotides, ribonucleotides, alpha-anomeric forms thereof, and the like. A polynucleotide can be composed entirely of deoxyribonucleotides, ribonucleotides, or analogs thereof, or can contain blocks or mixtures of two or more different monomer types. Usually nucleoside monomers are linked by phosphodiester linkages. However, polynucleotides and oligonucleotides containing non-phosphodiester linkages are also contemplated. "Polynucleotide" also encompasses polymers that contain one or more non-naturally occurring monomers and/or intersubunit linkages, such as peptide nucleic acids (PNAs), L-DNA, RNA, peptides, and analogs thereof. Polynucleotides typically range in size from a few monomeric units, e.g. 8-40, to several thousand monomeric units. An electrochemical probe including a polynucleotide can include a polynucleotide having a size range of up to about 125 monomeric units, and can be from about 8 to about 65 monomeric units.

"Siderophore" refers to small metal-chelating molecules produced by certain bacteria to facilitate transport of iron into a cell for cellular metabolic functions. While iron is abundant in the soil where these organisms live, the very low aqueous solubility of ferric iron ($10^{-18}$ M) necessitates that these organisms employ an efficient iron chelator as a solubilizing agent to take up ferric iron. Siderophores contain one or more bidentate chelating groups which will form a soluble and stable octahedral $Fe^{3+}$ complex. In cases where three bidentate groups are present and suitably distributed in the siderophore, one molecule will enclose the $Fe^{3+}$ providing all the ligands for the octahedral complex. While not their natural function, siderophores are also capable of forming complexes with other metal $3^+$ ions of row four of the periodic table (the first transition row) similar in size to iron, such as $Cr^{3+}$, $Mn^{3+}$, and $Ni^{3+}$. While the bidentate functional groups present in siderophores are excellent ligands for many transition metals, larger ions such as $Mo^{3+}$ and $Ru^{3+}$ and particularly those of the second transition row can generally be too large to be fully complexed by bacterial siderophores due to steric constraints and other factors.

The present teachings include tri-nuclear metal complexes of osmium and ruthenium or another metal, or a salt thereof, non-cleavable and cleavable probes labeled with a tri-nuclear complex of osmium or ruthenium or another metal, or a salt thereof, nucleic acid amplification methods, sequencing reactions, kits for polynucleotide amplification that include a probe labeled with a tri-nuclear osmium, ruthenium or other metal complex, or a salt thereof, and methods for preparing tri-nuclear osmium, ruthenium or other metal complexes, or a salt thereof. The tri-nuclear metal complexes, or salts thereof, as disclosed herein can be synthesized from various siderophore starting materials. It should be noted that throughout this disclosure there are set forth a number of possible counterions for use with the tri-nuclear metal complexes disclosed herein. Although some specific counterions are set forth as exemplary, one skilled in the art based on the disclosure herein will recognize that there are other suitable counterions and that the counterions listed herein should not be viewed as limiting. Additionally, although generally referred to herein as "tri-nuclear metal complex" or the like, this terminology is intended to include not only the tri-nuclear metal complexes themselves, but also any possible salts thereof as tri-nuclear metal salt complexes.

The tri-nuclear metal complex (such as a tri-nuclear osmium complex, for example) prepared from siderophores is suitable for use as electrochemical labels in DNA sequencing probes that can optionally be cleavable. In electrochemical TaqMan® probes, the non-hybridized 5'-portion (flap) of the probe (with the attached electrochemical label) is cleaved off by a polymerase and then captured by a complementary capture oligonucleotide attached to an electrode, wherein a measurable electrochemical signal is generated and detected. Employing natural, D-DNA for the entire probe length can, in some cases, complicate the analysis due to unforeseen cross-hybridization of the full-length (uncleaved) probe to unintended target sites. This can be avoided by substitution of L-DNA nucleotides for most of the natural D-DNA in the flap sequence during automated synthesis of the full-length probe. The corresponding capture oligonucleotide on the electrode is entirely L-DNA. The target D-DNA can not interact with the synthetic L-DNA oligonucleotides and, as such, cross-hybridization events are less likely to occur. Additionally, probes including the electrochemical label are also suitable for multiplexing where there are multiple electrodes present in the system and each has a specific capture oligonucleotide.

As disclosed herein, the tri-nuclear electrochemical label can be coupled to an oligonucleotide to form a suitable non-cleavable or cleavable probe in a single coupling step, or in other multiple coupling steps in order to couple multiple tri-nuclear complexes to a single oligonucleotide. The tri-nuclear electrochemical label can be detected by an electrochemical detection method, such as a voltammetric detection method, a potentiometric detection method, an amperometric detection method, an electrochemiluminescence method, a fluorescence method, or other suitable method used in conjunction with a polynucleotide amplification process, ligation-based sequencing process, or other suitable process. The tri-nuclear metal complexes disclosed herein can provide an electrochemical signal, or other signal, upon detection that is synergistic in nature; that is, the signal provided by a single tri-nuclear metal complex is not simply additive, but geometrical in nature as compared to a single-nuclear metal complex, such as single nuclear osmium complex. When a tri-nuclear metal complex is utilized as an electrochemical label on a non-cleavable or cleavable probe, the electrochemical signal is potentially several times greater than that of a probe that includes only a single-nuclear complex. Additionally, higher order labeling can be utilized with the electrochemical labels of the present teachings wherein a probe can comprise 2, 3, 4, 5, 6, 7 or even more tri-nuclear complexes such that the probe includes 6 (2×3), 9 (3×3), 12 (4×3), 15 (5×3), 18 (6×3), 21 (7×3), or even more metals in a tri-nuclear complexed form; stated another way, more than one tri-nuclear metal complex can be attached to an oligonucleotide probe in accordance with the present teachings to generate increased signals, such as increased electrochemical signals.

The tri-nuclear metal complexes as disclosed herein, and suitable for use as electrochemical labels, can comprise structure (I), (II), (III), or (IV), or a salt thereof:

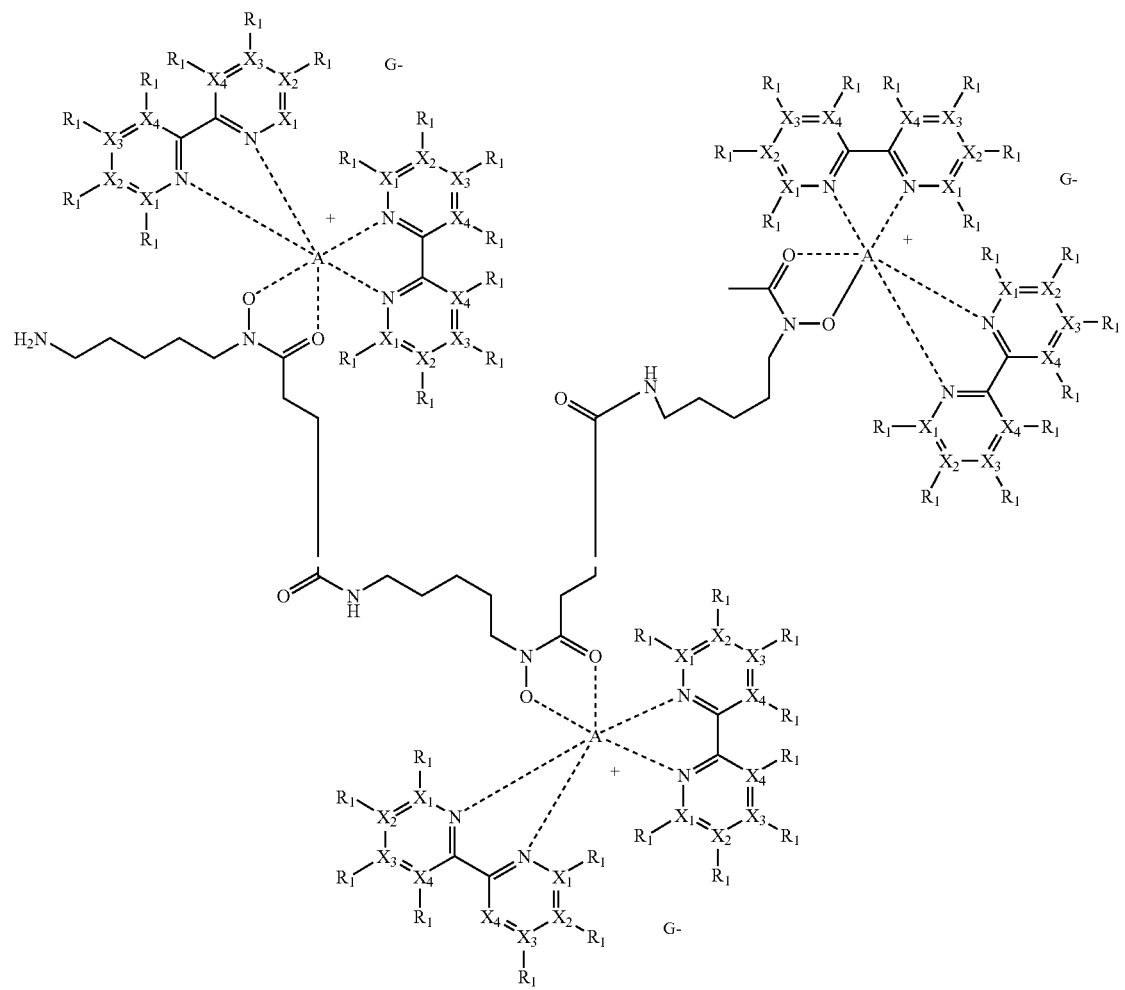
(I)
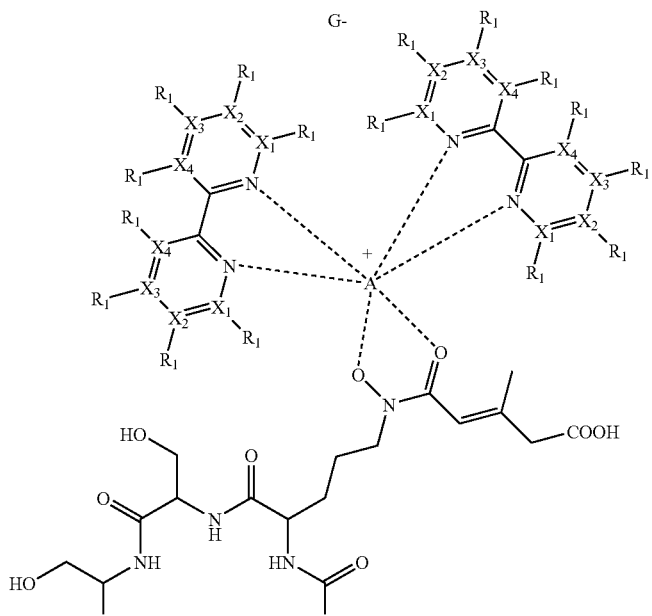
(II)

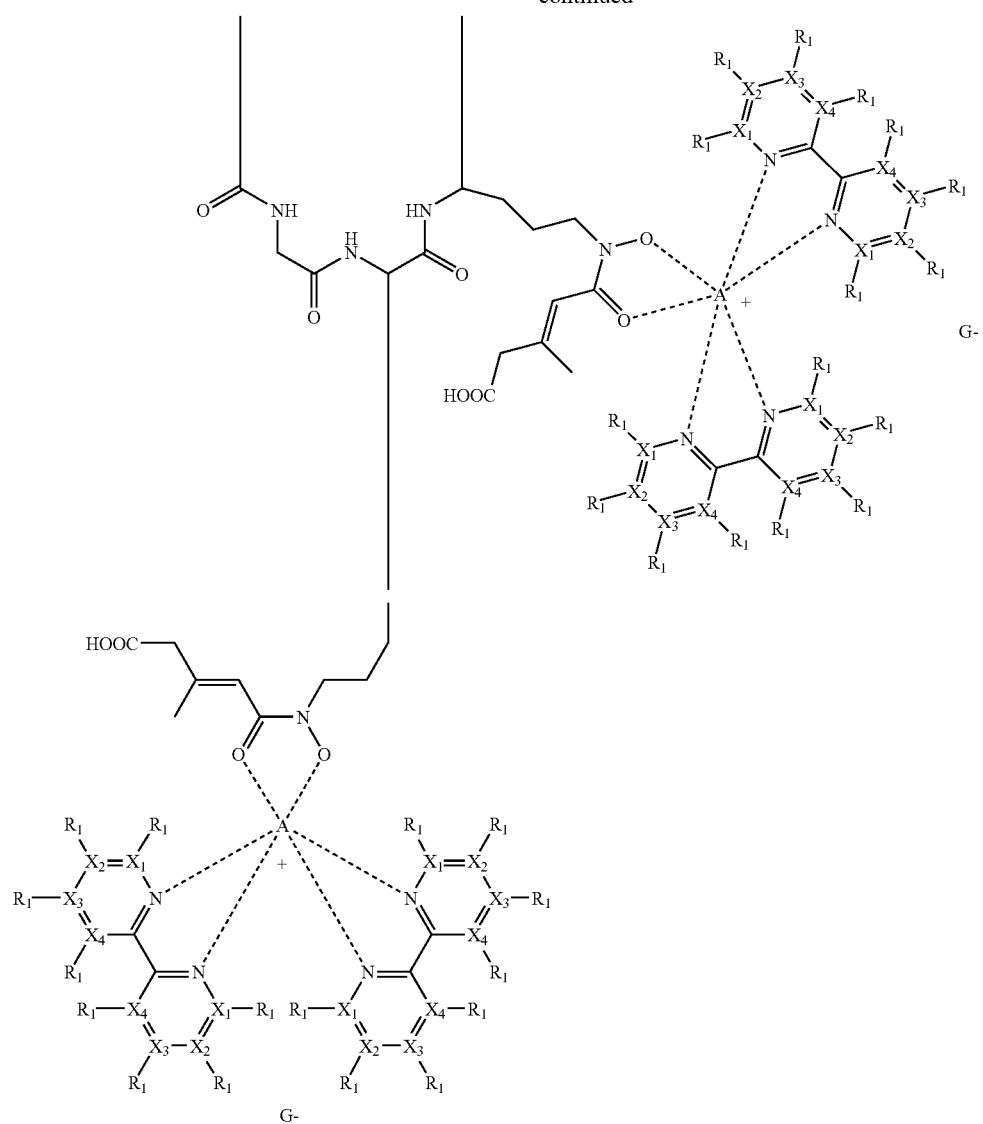

(III)
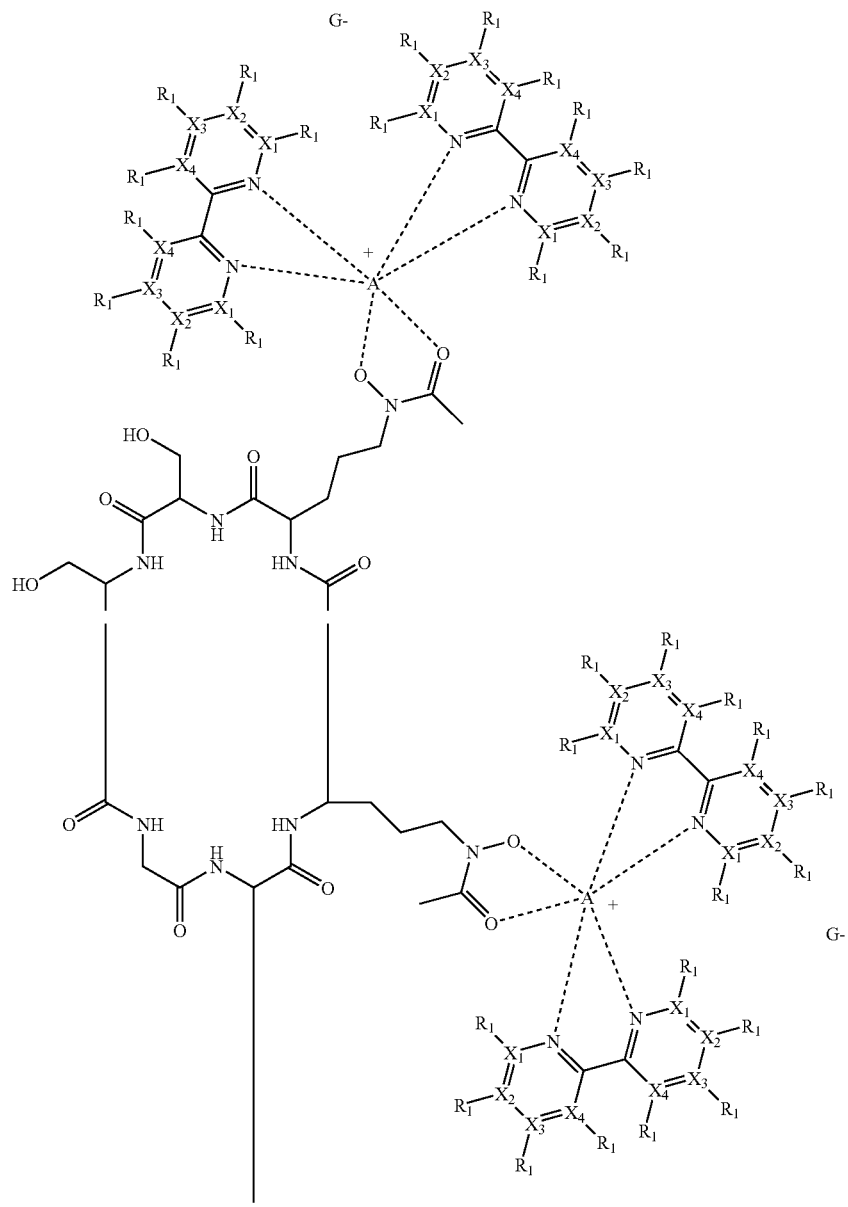

-continued

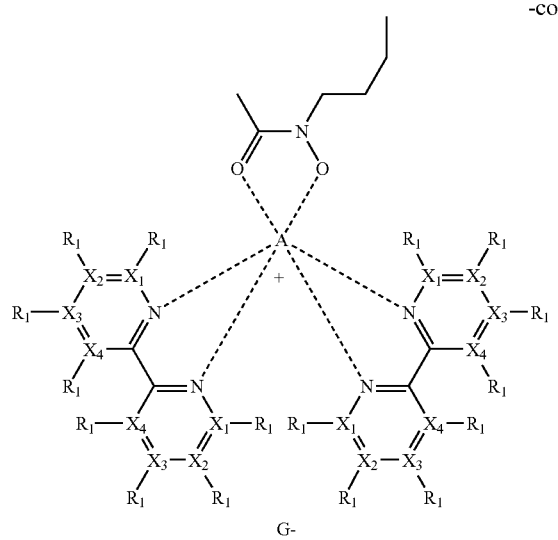

(IV)

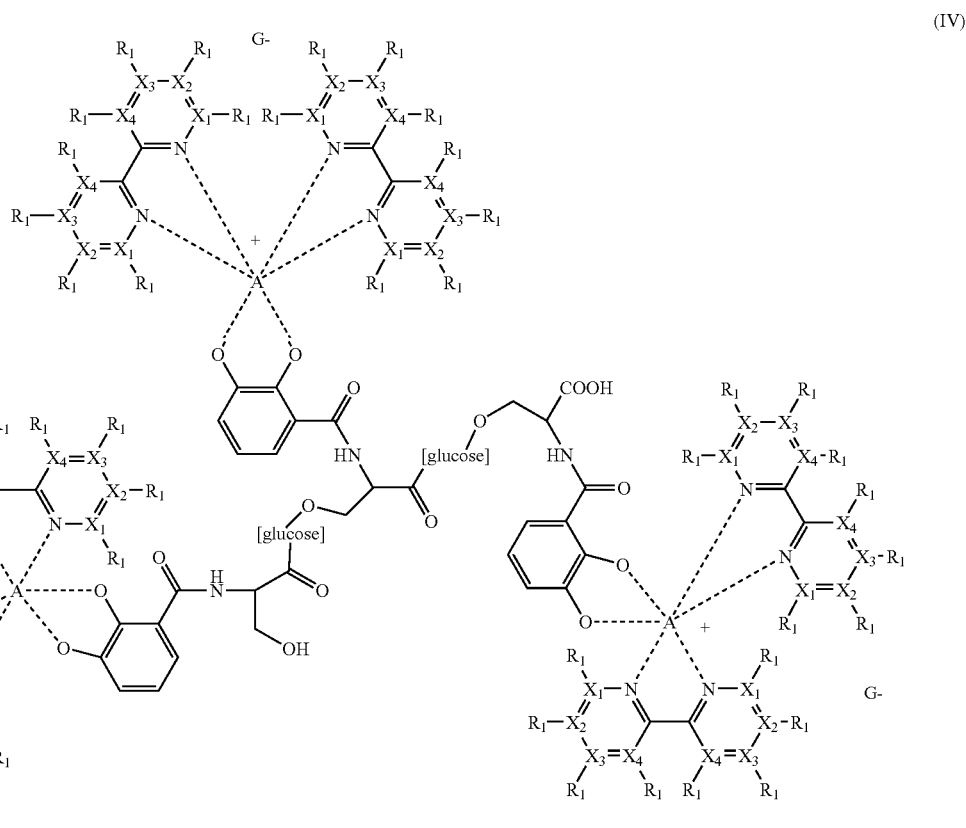

wherein:
A is Os, Ru, Fe, V, Cr, Mn, or Co;
$X^1, X^2, X^3, X^4$ are independently selected from C or N; when $X^1$ is N, the $R^1$ corresponding to that $X^1$ is omitted; when $X^2$ is N, the $R^1$ corresponding to that $X^2$ omitted; when $X^3$ is N, the $R^1$ corresponding to that $X^3$ is omitted; and when $X^4$ is N, the $R^1$ corresponding to that $X^4$ is omitted;
$R^1$ is H, $C_1$-$C_8$ alkyl, alkenyl or alkynyl and can be substituted with a hetero atom, $C_1$-$C_8$ substituted phenyl, alkoxy, alkylthio, $C_1$-$C_{10}$ N-alkylamino, N,N-dialkylamino, N,N,N-trialkylammonium, N-alkylaminocarbonyl, N,N-dialkylaminocarbonyl, alkylcarboxylamino, fluoro, chloro, bromo, iodo, fluoroalkyl, chloroalkyl, bromoalkyl, iodoalkyl, O-alkylcarbamoyl, N-alkylcarbamoyl, nitro, cyano, carboxyl, formyl, alkylcarbonyl, alkoxycarbonyl, hydroxyl, hydrazido, aryl or aryl alkyl; and
$G^-$ is a monovalent counterion that can be selected from $PF_6^-$, $TFA^-$, $OAc^-$, $Cl^-$ and $Br^-$.

In some embodiments of the present teachings, the trinuclear metal complex can comprise the structure (I'), (II'), (III'), or (IV'), or a salt thereof:

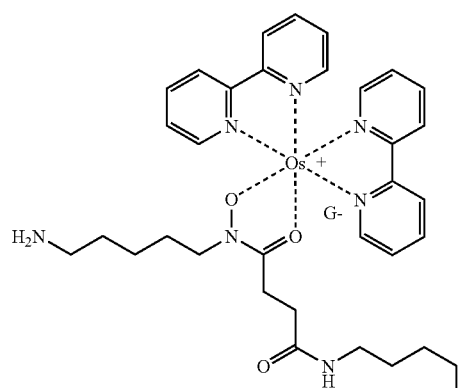
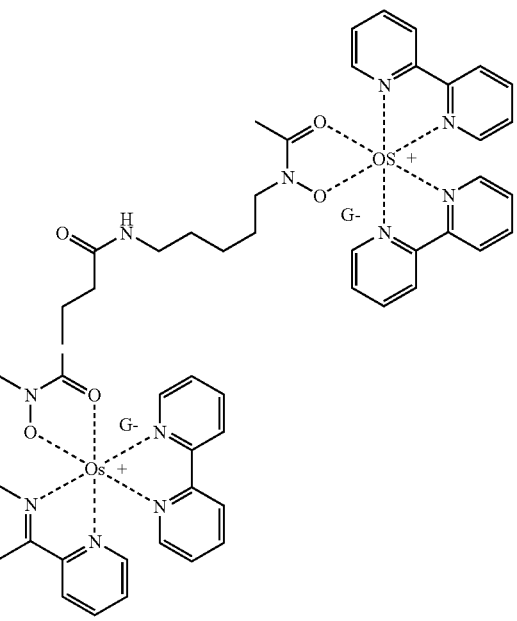
(I')
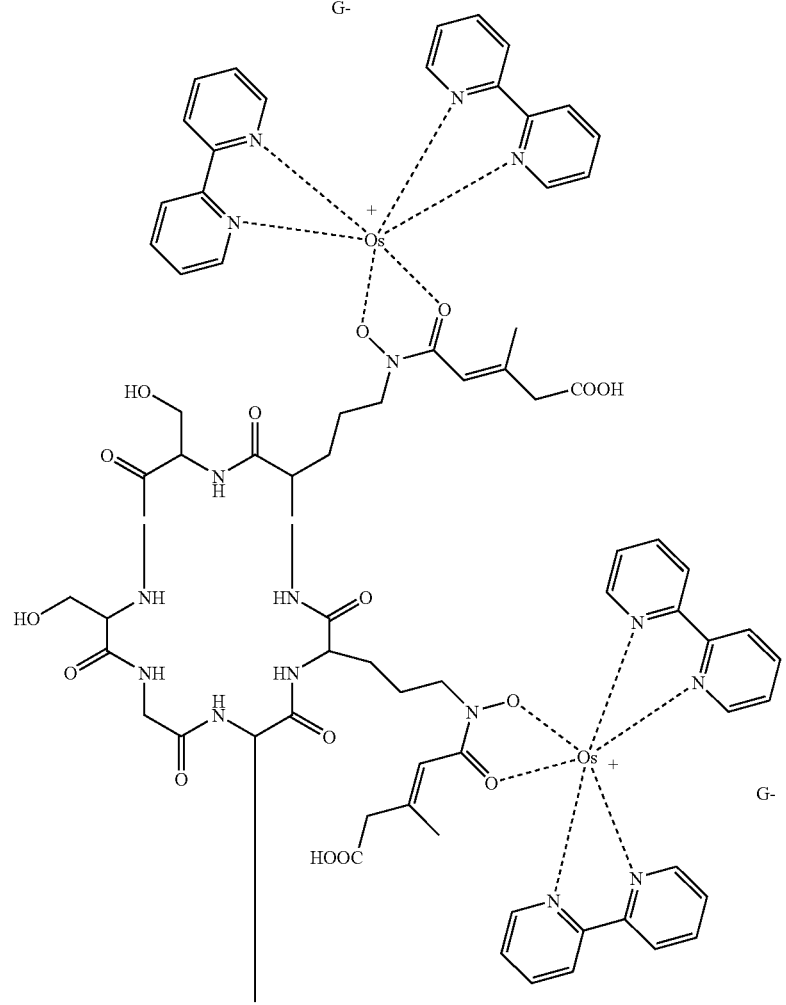
(II')

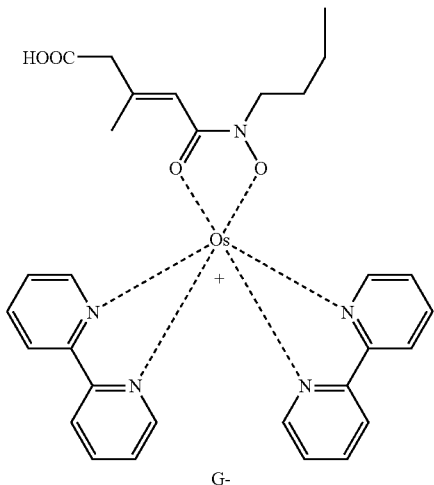
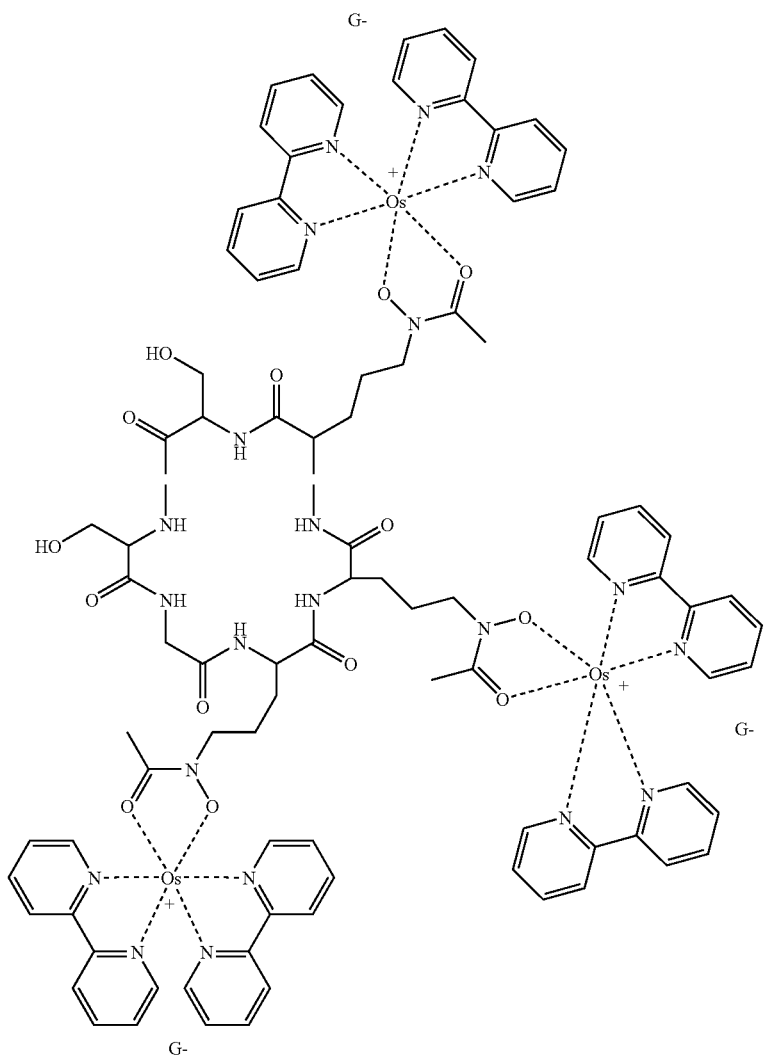
(III')

-continued

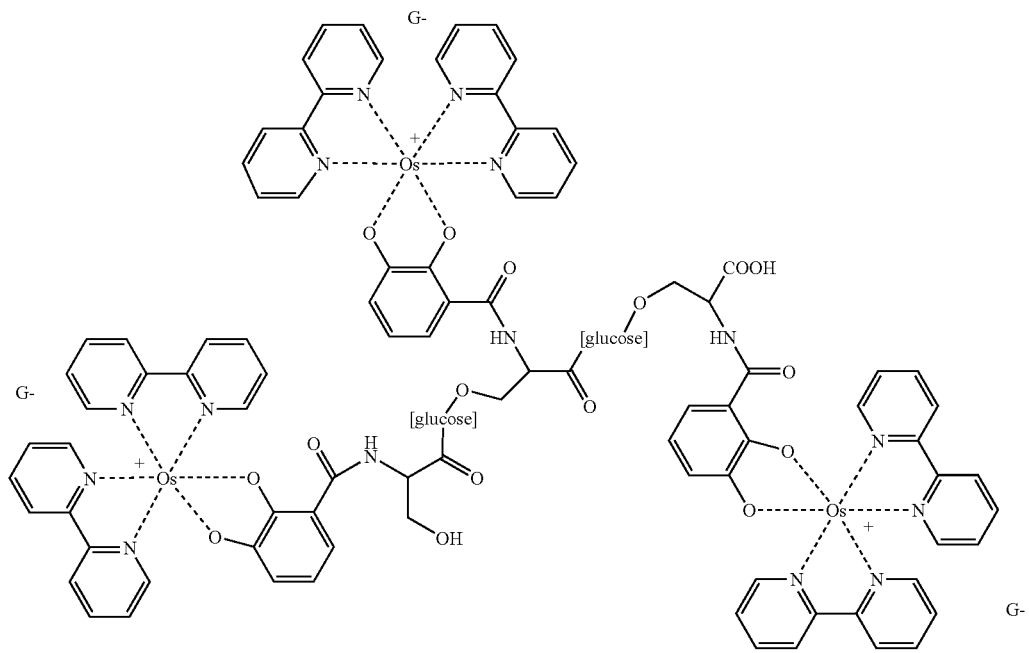

(IV')

wherein G⁻ is a counterion as discussed herein. One of ordinary skill in the art based on the disclosure herein would understand that in each of the structures I', II', III', and IV' or salts thereof, that Os can be replaced with Ru, Fe, V, Cr, Mn, or Co.

Figure 2:
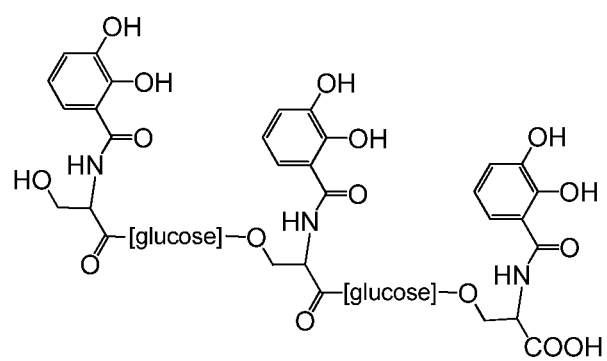

The tri-nuclear metal complexes of the present teachings can be synthesized utilizing siderophores as starting materials. Siderophores are natural products and allow for the synthesis of tri-nuclear metal complexes without the technical difficulties of synthesis of polyacetoacetonates, polyhydroxamates and/or polycatecholates. Some examples of suitable siderophore starting materials include, for example, desferrioxamine B, desferrichrome A, desferrirhodin, and salmochelin 2. Structures for these four siderophores are shown in FIGS. 1 and 2. In some embodiments of the present teachings, a tri-nuclear osmium complex suitable for use as an electrochemical label can be prepared by reacting the siderophore with bis(bipyridyl)carbonato Os(II), which can be prepared from commercially available bis(bipyridyl)dichloroosmium (II). The chloro groups on the osmium are replaced with water molecules in order for the hydroxyamic acid groups to be chelated; this intermediate is generated in situ by contact of the carbonato complex with acidic media. The pH is then raised to about 10 and the siderophore is added. The hydroxamic acids are deprotonated and the osmium is complexed. The bis(bipyridyl) ligands in the starting complex are kinetically stable under these reaction conditions. The resulting tri-nuclear complex can be isolated by precipitation from aqueous solution by treatment with saturated KPF₆, or another suitable reagent to provide an appropriate counterion for the charged complexes. The resulting product can optionally then be redissolved in a chlorinated solvent and precipitated by the addition of hexane to obtain an essentially pure tri-nuclear osmium material. Optionally, the resulting complex can be purified by preparative RP-HPLC. A specific method of preparation of a tri-nuclear osmium complex in accordance with the present disclosure is set forth below in the Examples. From the disclosure herein, one skilled in the art would recognize that the above-noted synthesis route can be modified to incorporate other metals, such as Ru, Fe, V, Cr, Mn or Co into the metal complexes in place of Os.

Figure 6:
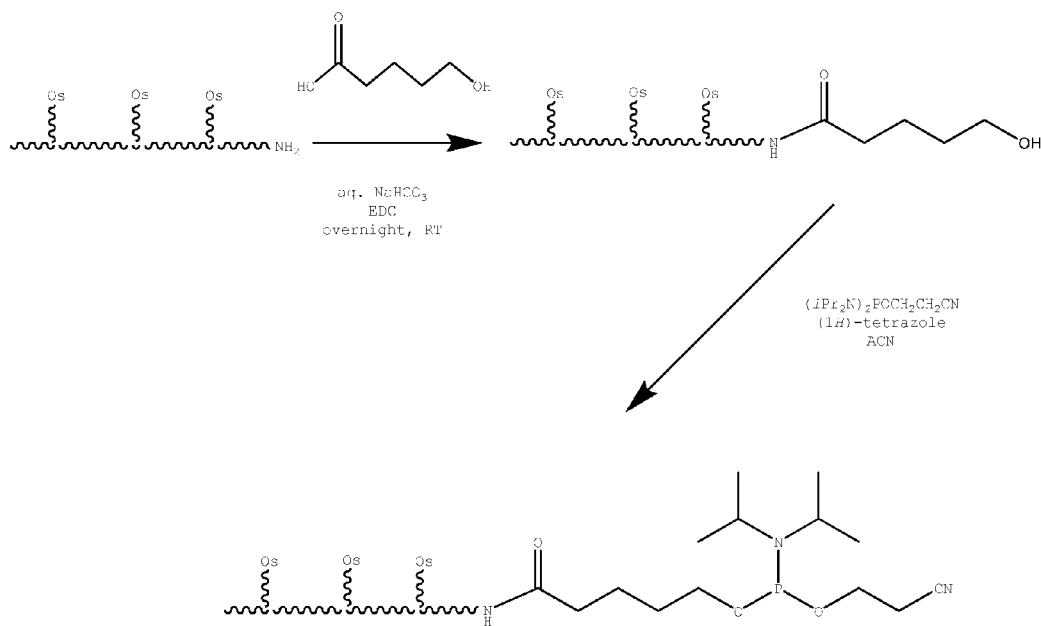

The synthesized tri-nuclear metal complexes can be incorporated as electrochemical labels into a non-cleavable or cleavable probe suitable for use in a DNA amplification process or sequencing process in a single coupling step, or in multiple coupling steps. In some embodiments of the present disclosure, a tri-nuclear metal complex can be reacted with a cyclic dicarboxylic acid anhydride, such as glutaric anhydride, for example, to generate an amide linkage and a free carboxylic acid group. HPLC purification can be utilized to purify the resulting compound and prepare it for conjugation to an amine-modified oligonucleotide probe using HBTU, HATU, or other conventional uronium-type coupling reagents. The resulting electrochemical labeled oligonucleotide probe can be purified by RP-HPLC. Alternatively, following osmium complexation, the free terminal amino group of the siderophore can be acylated with a hydroxylated linker, and then phosphitylated by the conventional approach to enable 5'-labeling of probes on a DNA synthesizer via a CE-phosphoramidite. A specific method of preparation of an electrochemically labeled oligonucleotide probe in accordance with the present disclosure is set forth below in the Examples. An example of this route is shown in FIG. 6.

Some exemplary cleavable probes incorporating the tri-nuclear metal complexes described herein are set forth below as structures (V), (VI), (VII), and (VIII), which can also be in salt form:

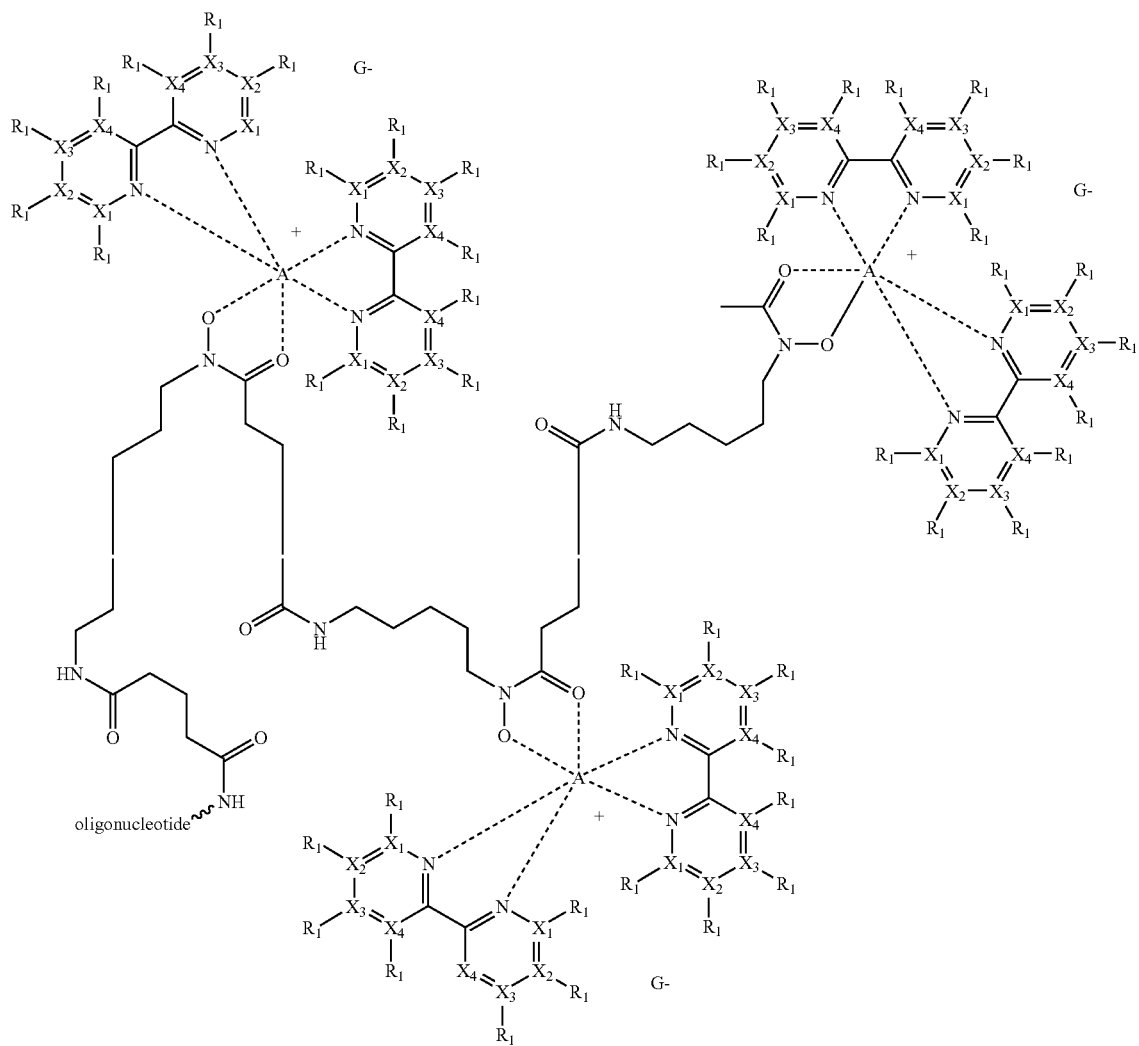
(V)
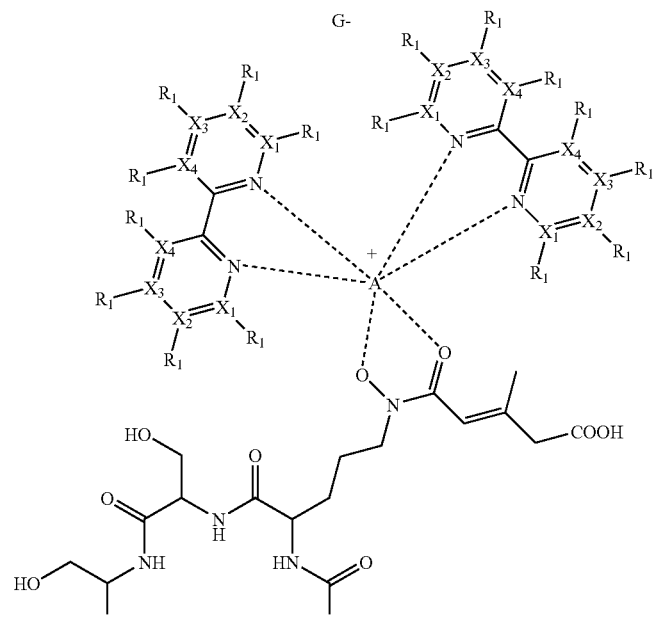
(VI)

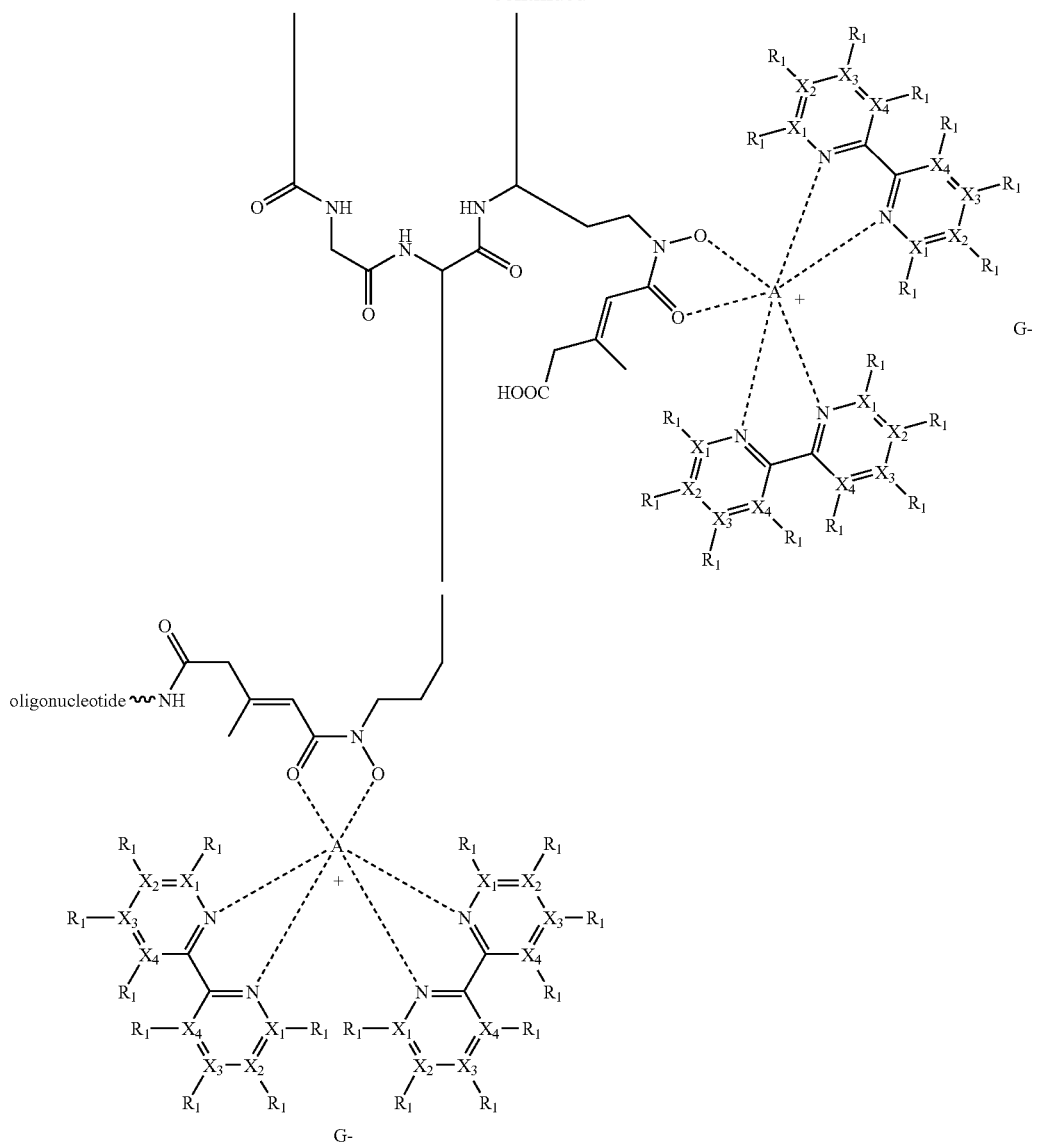

(VII)
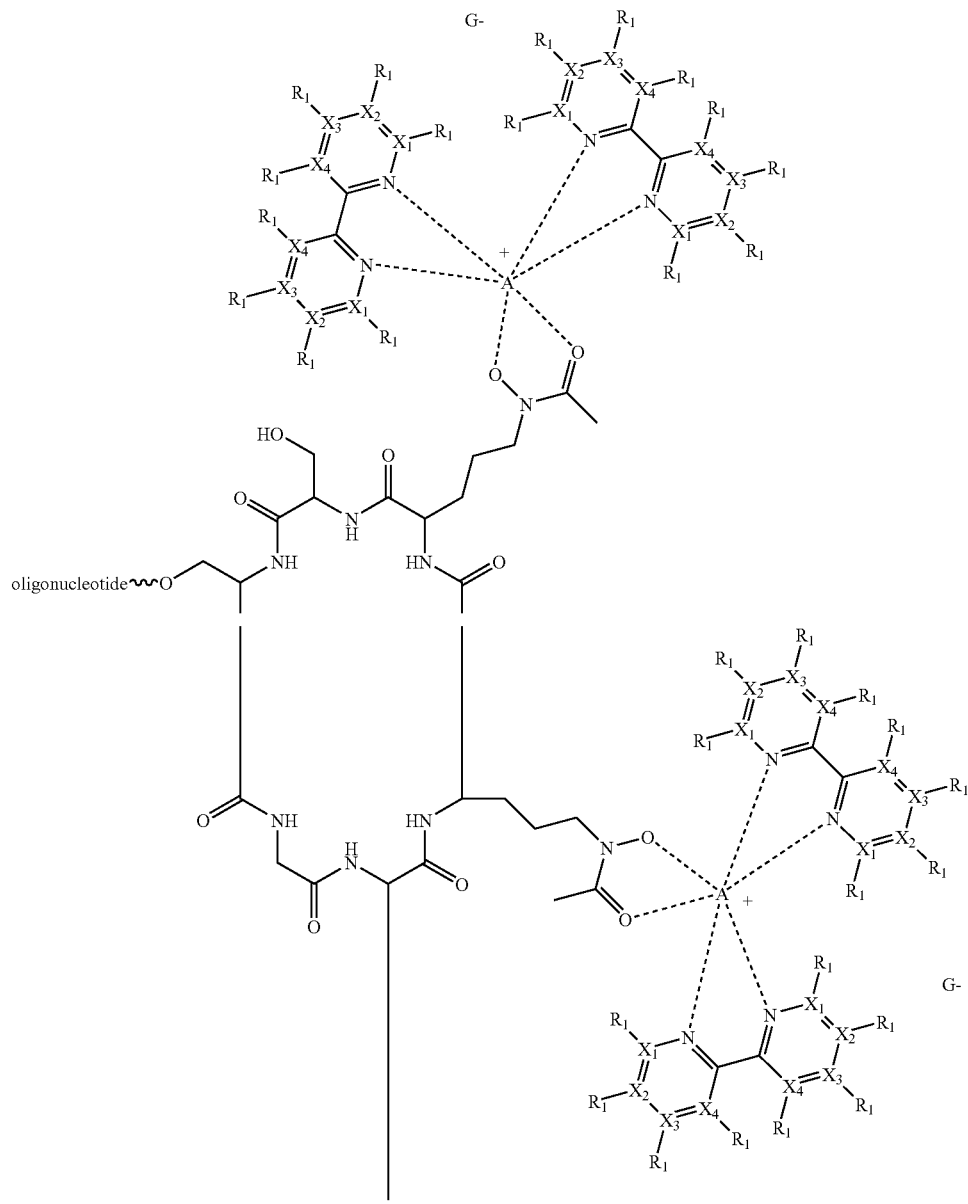

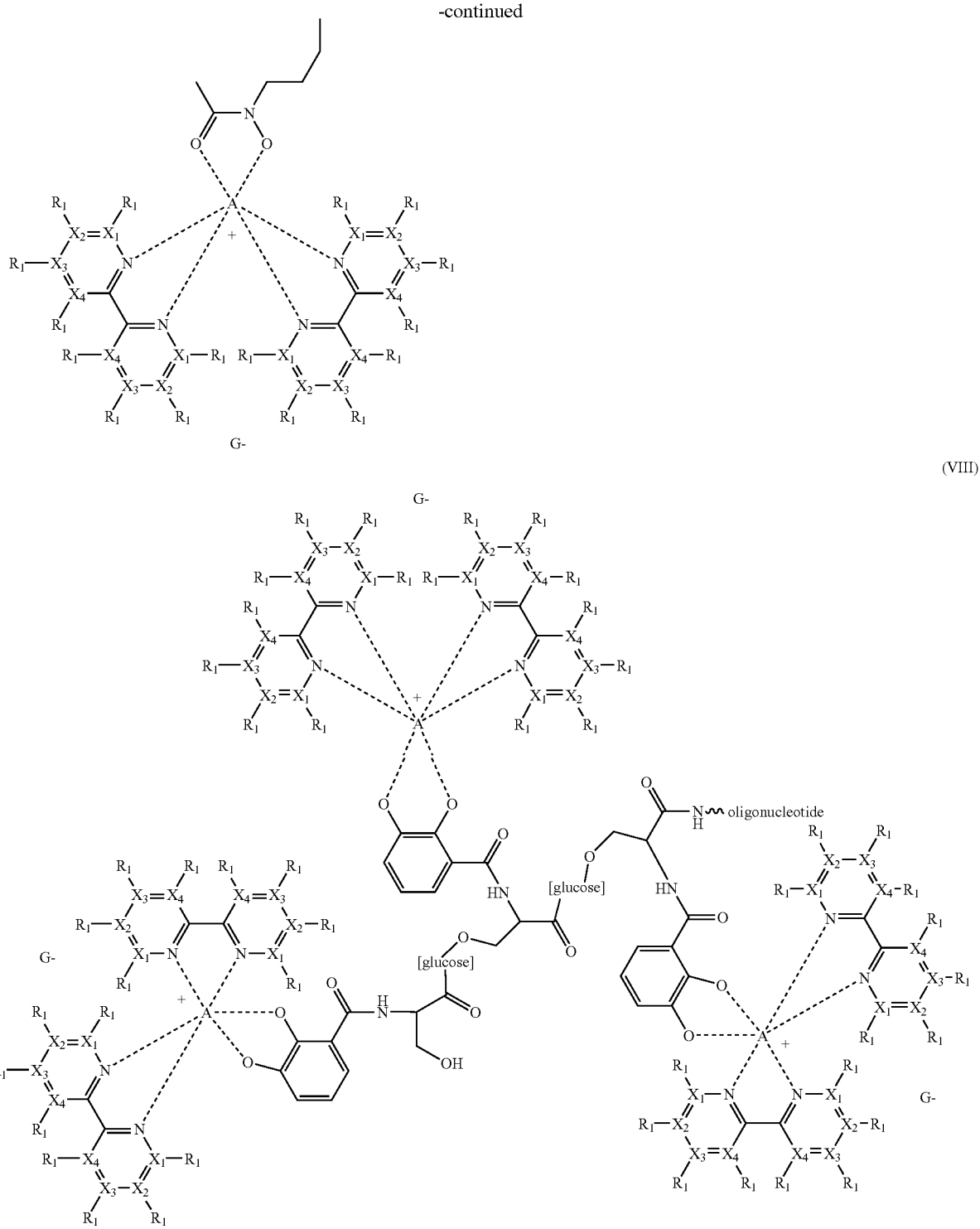

wherein
A is Os, Ru, Fe, V, Cr, Mn, or Co;
$X^1, X^2, X^3, X^4$ are independently selected from C or N; when $X^1$ is N, the $R^1$ corresponding to that $X^1$ is omitted; when $X^2$ is N, the $R^1$ corresponding to that $X^2$ omitted; when $X^3$ is N, the $R^1$ corresponding to that $X^3$ is omitted; and when $X^4$ is N, the $R^1$ corresponding to that $X^4$ is omitted;
$R^1$ is H, $C_1$-$C_8$ alkyl, alkenyl or alkynyl and can be substituted with a hetero atom, $C_1$-$C_8$ substituted phenyl, alkoxy, alkylthio, $C_1$-$C_{10}$ N-alkylamino, N,N-dialkylamino, N,N,N-trialkylammonium, N-alkylaminocarbonyl, N,N-dialkylaminocarbonyl, alkylcarboxylamino, fluoro, chloro, bromo, iodo, fluoroalkyl, chloroalkyl, bromoalkyl, iodoalkyl, O-alkylcarbamoyl, N-alkylcarbamoyl, nitro, cyano, carboxyl, formyl, alkylcarbonyl, alkoxycarbonyl, hydroxyl, hydrazido, aryl or aryl alkyl;

G⁻ is a monovalent counterion that can be selected from $PF_6^-$, $TFA^-$, $OAc^-$, $Cl^-$ and $Br$; and ∼∼∼ is a linker between the electrochemical label and an oligonucleotide.

The electrochemical labels as described herein generally have a redox couple that is reversible, and both oxidation states of the electrochemical label are generally substantially chemically inert at conditions typical for DNA amplification processes and DNA synthesis processes, including elevated temperatures. Additionally, the electrochemical labels generally have a redox couple that does not substantially overlap with the oxidation or reduction potentials of the DNA being amplified or with any of the components generally present in DNA detection assays, including dithiothreitol (DTT), water, other buffer components, and polymerases. In some embodiments, the electrochemical labels have an $E_{1/2}$ of from about −200 to about 500 mV vs. Ag/AgCl, even from about −80 to about 265 mV vs. Ag/AgCl, or even −100 to about 0 mV vs. Ag/AgCl.

It is generally desirable that the electrochemical labels not interact substantially with the conjugate DNA in a base-specific manner, nor intercalate into DNA duplexes. The electrochemical or other signal generated by the electrochemical labels as described herein upon cleavage are generally consistent, regardless of the DNA sequence being amplified. Additionally, the electrochemical labels of the present teachings are readily incorporated into oligonucleotide probes as discussed herein, and the addition of the electrochemical labels does not significantly alter the physicochemical properties of the DNA, such as high aqueous solubility and ability to readily re-dissolve following dehydration.

The present teachings also include kits for performing various methods disclosed herein. For nucleic acid amplification, one suitable kit includes at least one electrochemically-labeled oligonucleotide probe as disclosed herein. The kit can additionally include first and second primers, polymerases, other non-labeled oligonucleotides, nucleotides, buffering agents, etc.

Based on the teachings herein, it will be recognized by one of ordinary skill that the moieties coordinated to the metal in the electrochemical labels described herein (the bis-biheterocycles) can optionally be replaced with other suitable ligands within the scope of the present disclosure to produce electrochemical labels suitable for use as described herein. For example, one or both of the bis-biheterocycles described herein can optionally be replaced with a 2,2'biimidazole and ring substituted derivatives thereof, a [2,2',4,4'-bi(1,2,4-triazole)] and ring-substituted derivatives thereof, a 2,2'-bioxazole, a 2,2'-bipyrazine, a 2,2'-bi-1,3,5-triazine, a 2-(2'-pyridyl)imidazole, and any other dimer of two differing nitrogen heterocycles where a nitrogen is present on each aromatic heterocycle in the position adjacent to the two bridging carbons.

Aspects of the present teachings can be further understood in light of the following examples, which should not be construed as limiting the scope of the present teachings in any way.

EXAMPLE 1

In this Example, a tri-nuclear osmium (II) complex was synthesized from the siderophore desferrioxamine B sulfate.

Figure 3:
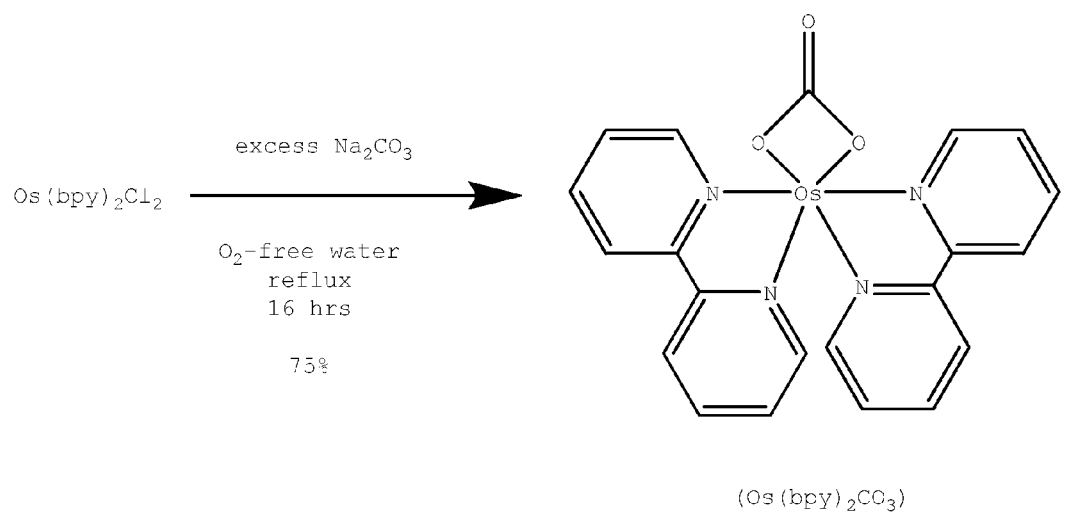
FIG. 3 shows a synthesis route for preparing bis(2,2'-bipyridinyl)carbonatoosmium(II).

First, bis(2,2'-bipyridyl)carbonatoosmium(II) was prepared. Deionized water (40 mL) was degassed under vacuum and then sparged with argon throughout the synthesis procedure. Bis(2,2'-bipyridyl)dichloroosmium(II) (Colonial Metals, Elkton, Md.) (0.50 grams, 0.87 mmol) and 2.0 grams sodium carbonate (Sigma-Aldrich, St. Louis, Mo.) was added to the deionized water. The resulting solution was heated to reflux for 2 hours, cooled slightly, and then another 2.0 grams of sodium carbonate was added and the reflux period repeated, and then another 2.0 grams of sodium carbonate (for a total of 6.0 grams of sodium carbonate) was added and the reflux period again repeated. The solution was allowed to come to ambient temperature overnight under argon. Fine crystals were collected on a glass frit and washed with oxygen-free water (40 mL, pH adjusted to 10 with carbonate solution), and then washed with ether (40 mL). The resulting product was then dried in a vacuum oven for 6 hours at 70° C. The yield was 0.42 grams (81% theoretical, as the dihydrate). A synthesis route for preparing the bis(2,2'-bipyridyl)carbonatoosmium(II) is shown in FIG. 3.

Figure 4:
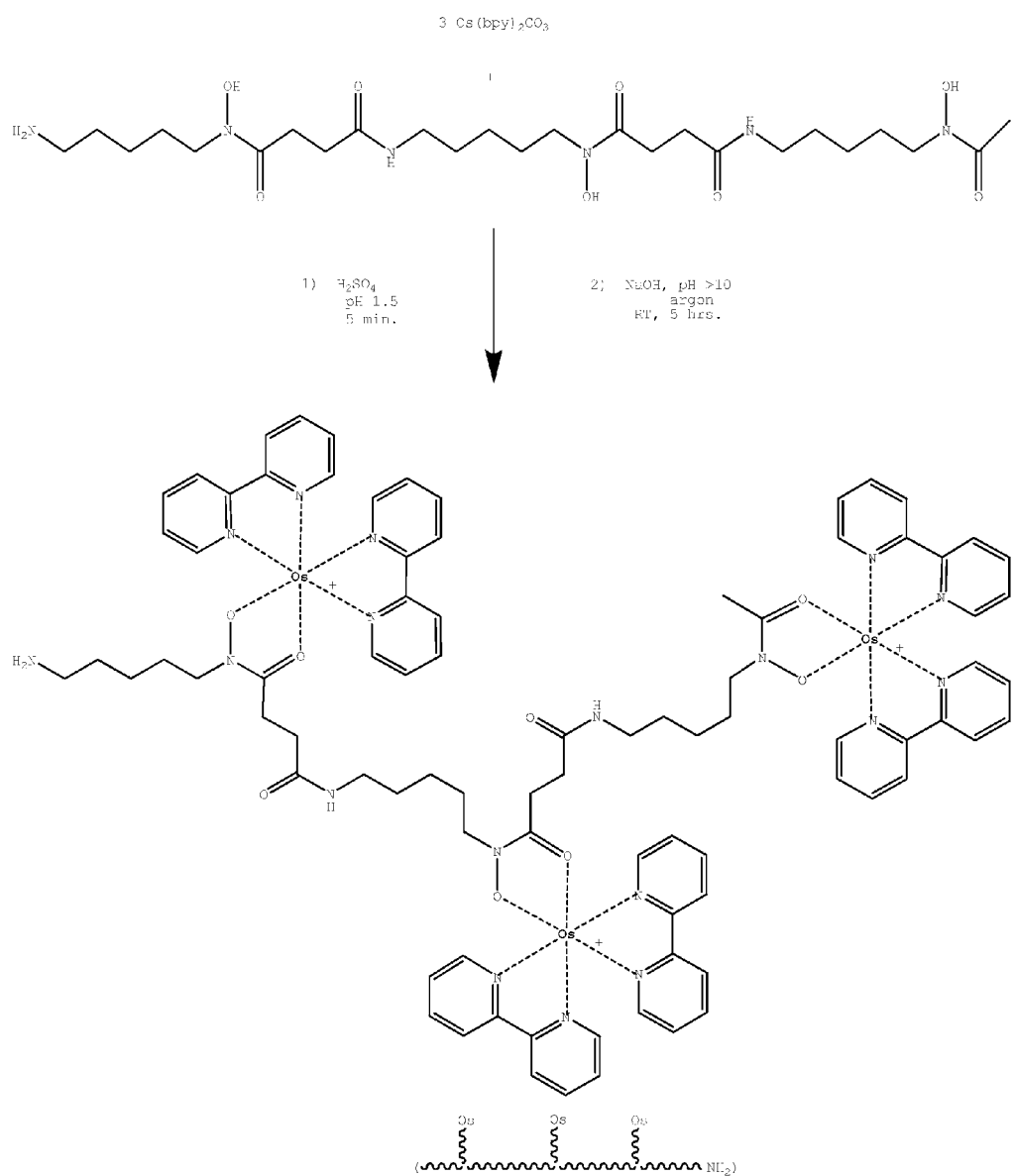
FIG. 4 shows a synthesis route for preparing a tri-nuclear osmium complex.

Bis(2,2'-bipyridyl)carbonatoosmium(II) (0.34 grams, 0.60 mmol) was added to a flask containing oxygen-free water (60 mL) and the flask was fitted with an argon bubbler and pH electrode. The mixture was stirred under a continuous argon stream and sulfuric acid (6 mL of 2N) was added and produced a deep red-violet solution. Separately, a solution of desferrioxamine sulfate (EMD-Calbiochem, San Diego, Calif.) (118 milligrams, 0.18 mmol) in degassed sodium hydroxide (4 mL of 2N) was prepared, and the osmium solution introduced thereto. Sodium hydroxide (2 mL) was added to achieve a solution pH of 10. After stirring for six hours, the reaction mixture was treated with a saturated solution of $KPF_6$ (120 mL) to achieve a pH of 7. The solution was then allowed to stand undisturbed for several hours to allow fine purple-black crystals to form. The crystals were then collected. These crystals were then dissolved in dichloromethane (300 mL), washed twice with water, and then dried over $Na_2SO_4$. The solution volume was then reduced to 100 mL, hexane was added (400 mL), and the mixture was chilled to produce fine purple crystals as the tris(hexafluorophosphate) salt of the tri-nuclear osmium complex. A synthesis route for preparing the tri-nuclear osmium complex is shown in FIG. 4.

EXAMPLE 2

In this Example, an oligonucleotide was labeled with the tri-nuclear osmium complex prepared in Example 1.

First, a carboxyl linker was attached to the tri-nuclear osmium (II) complex. A solution was prepared including the tri-nuclear osmium complex of Example 1 (0.225 grams, 0.10 mmol), sodium bicarbonate (10 mL, 0.25M, pH of 8.3), and dioxane (5 mL). This solution was added to a solution of glutaric anhydride (23 milligrams, 0.20 mmol) in dioxane (5 mL). This mixture was stirred overnight, and water (20 mL) was added. The resulting solution was then neutralized with ammonium chloride (2N) and washed with ether. The aqueous layer was concentrated to 10 mL and the product was purified by preparative RP HPLC (C18, gradient 5-65% ACN in 0.1 triethylammonium acetate, 1 mL/min, 30 minutes). Following isolation, the resulting tri-nuclear osmium (II) complex with the carboxyl linker was lyophilized.

The tri-nuclear osmium (II) complex with the carboxyl linker was then coupled to an oligonucleotide to synthesize a labeled oligonucleotide. An oligonucleotide with an amine modification at the 5' end was obtained. Salt exchange by ethanol precipitation was done to remove traces of ammonia, TRIS, or other reactive amines that can be present from the synthesis and/or purification of the oligonucleotide.

Figure 5:
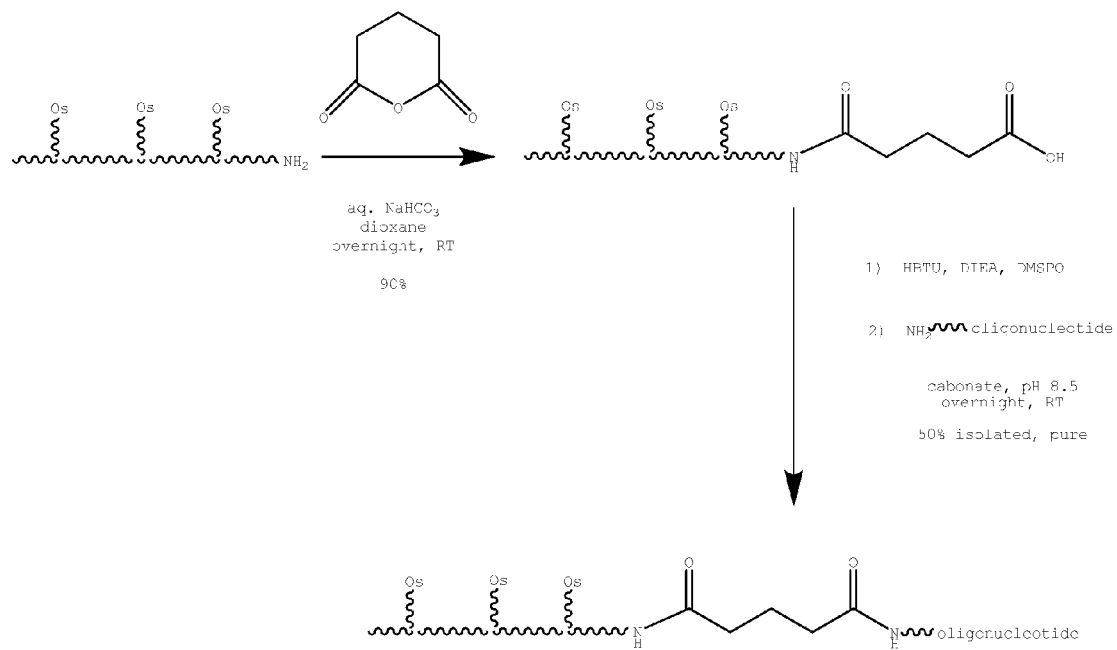
FIGS. 5 and 6 show synthesis routes for preparing oligonucleotide probes having an electrochemical label.

The tri-nuclear osmium (II) complex with the carboxyl linker was volumetrically dispensed into 300 nmol aliquots and dried. An activation solution consisting of HBTU (38 milligram, 0.10 mmol) and DIEA (52 microliters, 0.3 mmol) dissolved in DMSO (1 mL) was prepared. An aliquot of the osmium (II) complex (300 nmol) was dissolved in DMSO (3 microliters) and treated with seven microliters of the activation solution, vortexed briefly and allowed to stand. After 10 minutes, this solution (10 microliters) was added to a solution of the amino-oligonucleotide (20 nmol) in sodium bicarbonate (20 microliters of 0.25M) at a pH of 8.3. The mixture was vortexed gently overnight and the resulting labeled oligonucleotide was ethanol precipitated and purified by RP HPLC to yield 10 nmol. A synthesis route for preparing the labeled oligonucleotide is shown in FIG. 5.

What is claimed is:

1. The tri-nuclear metal complex comprising structure (I'), or a salt thereof:

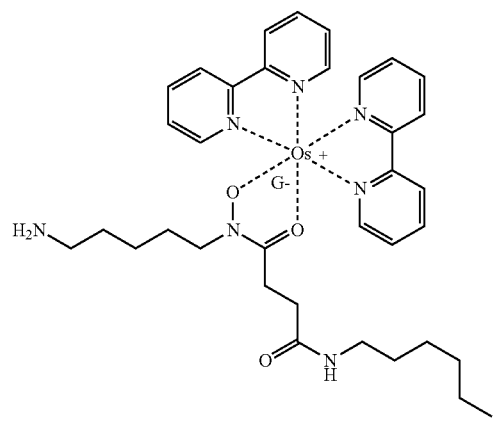

(I')

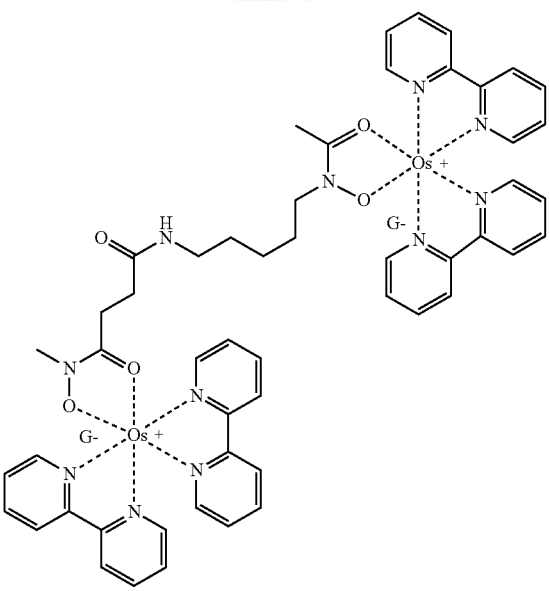

wherein G" is a monovalent counterion.

2. The tri-nuclear metal complex of claim 1, wherein the tri-nuclear complex has an $E_{1/2}$ value of from about −200 to about 500 mV vs. Ag/AgCl.

3. The tri-nuclear metal complex of claim 1, wherein the counterion is selected from the group consisting of $PF_6^-$, $TFA^-$, $OAc^-$, $Cl^-$ and $Br^-$.

* * * * *